US010329284B2

(12) United States Patent
Burk et al.

(10) Patent No.: US 10,329,284 B2
(45) Date of Patent: Jun. 25, 2019

(54) ESTER PRODRUGS OF GAMMA-LACTAMS AND THEIR USE

(71) Applicant: ALLERGAN, INC., Irvine, CA (US)

(72) Inventors: Robert M. Burk, Laguna Beach, CA (US); Wha Bin Im, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 15/516,361

(22) PCT Filed: Oct. 2, 2015

(86) PCT No.: PCT/US2015/053865
§ 371 (c)(1),
(2) Date: Mar. 31, 2017

(87) PCT Pub. No.: WO2016/054596
PCT Pub. Date: Apr. 7, 2016

(65) Prior Publication Data

US 2017/0298050 A1 Oct. 19, 2017

Related U.S. Application Data

(60) Provisional application No. 62/058,802, filed on Oct. 2, 2014.

(51) Int. Cl.

| | |
|---|---|
| ***C07D 409/06*** | (2006.01) |
| ***C07D 409/12*** | (2006.01) |
| ***A61K 9/00*** | (2006.01) |

(52) U.S. Cl.
CPC .......... *C07D 409/06* (2013.01); *A61K 9/0048* (2013.01); *C07D 409/12* (2013.01)

(58) Field of Classification Search
CPC .................................................... C07D 409/06
See application file for complete search history.

(56) References Cited

U.S. PATENT DOCUMENTS

| | | | |
|---|---|---|---|
| 3,149,954 | A | 9/1964 | Harrod |
| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 6,353,000 | B1 | 3/2002 | Sallee et al. |
| 9,024,042 | B2 | 7/2015 | Im et al. |
| 9,090,595 | B2 | 7/2015 | Im et al. |
| 9,427,401 | B2 | 8/2016 | Im et al. |
| 2005/0038287 | A1 | 2/2005 | Scherer et al. |
| 2007/0254920 | A1 | 11/2007 | deLong et al. |
| 2008/0015231 | A1 | 1/2008 | Old et al. |
| 2008/0269498 | A1 | 10/2008 | Old |
| 2009/0239869 | A1 | 9/2009 | Donde et al. |
| 2009/0270396 | A1 | 10/2009 | Old et al. |
| 2010/0210689 | A1 | 8/2010 | Old et al. |
| 2011/0124736 | A1 | 5/2011 | Trogden et al. |
| 2014/0057975 | A1 | 2/2014 | Im et al. |
| 2014/0171661 | A1 | 6/2014 | Burk et al. |
| 2015/0322036 | A1 | 11/2015 | Im et al. |

FOREIGN PATENT DOCUMENTS

| | | | |
|---|---|---|---|
| WO | 9605309 | | 2/1996 |
| WO | 2006047466 | | 5/2006 |
| WO | 2006063179 | A1 | 6/2006 |
| WO | 2006098918 | A2 | 9/2006 |
| WO | 2007109578 | A3 | 11/2007 |
| WO | 2008008718 | | 1/2008 |
| WO | 2009117388 | | 9/2009 |
| WO | 2009132088 | | 10/2009 |
| WO | 2009132097 | A1 | 10/2009 |
| WO | 2009140205 | A2 | 11/2009 |
| WO | 2011071620 | | 6/2011 |
| WO | 2011091276 | A1 | 7/2011 |
| WO | 2014031581 | | 2/2014 |
| WO | 2014035827 | | 3/2014 |
| WO | 2015175075 | | 11/2015 |

OTHER PUBLICATIONS

Shi, et al. Accession No. 2016:2036783, retrieved from STN; Jan. 17, 2013.*
Old, et al. Document No. 166:278068, retrieved from STN; Jun. 14, 2011.*
Gore, et al. Document No. 159:12312, retrieved from STN; Jun. 20, 2013.*
Cherkasov, Document No. 156:583, retrieved from STN; 2011.*
Robinson, et al. Document No. 153:465355, retrieved from STN; Sep. 30, 2010.*
Ghinet, et al. Document No. 152:191888, retrieved from STN; 2010.*
Old, et al. Document No. 151:508485, retrieved from STN; Oct. 29, 2009.*

(Continued)

*Primary Examiner* — Shawquia Jackson
(74) *Attorney, Agent, or Firm* — Jonathan Bass

(57) ABSTRACT

Described herein are ester prodrugs of gamma-lactam compounds of Formula (I): or pharmaceutically acceptable salt thereof, and methods of use of such compounds for the treatment of ocular diseases including, among other things, glaucoma and macular degeneration.

(I)

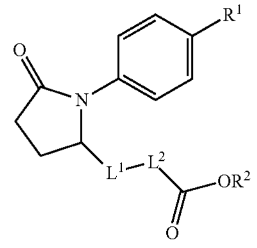

18 Claims, No Drawings

(56) References Cited

OTHER PUBLICATIONS

Ocular melanoma [online] retrieved from the internet on Sep. 4, 2017; http:www.webmd.com/cancer/ocular-melanoma.*

Abels, Falko et al, A General Strategy for the Catalytic, Highly Enantio-and Diastereoselective Synthesis of Indolizidine-Based Alkaloids, Chemistry—A European Journal, Feb. 2014, 1964-1979, 20(7).

Badarinarayana, Vivek, Studies Toward the Enantioselective Total Synthesis of the Martinella Alkaloids, Diss Abstr Int, 2006, 3133, 67(6), Database Accession No. 2007:464803.

Berge, Stephen M., Pharmaceutical Salts, Journal of Pharmaceutical Sciences, Jan. 1977, 1-19, 66 (1), US.

Cherkasov, Artem, Targeting the Binding Function 3 (BF3) Site of the Human Androgen Receptor Through Virtual Screening, Journal of Medicinal Chemistry, 2011, 8563-8573, 54(24), Database Accession No. 2011:1619070.

Frank D. King, Bioisosteres, Confirmational Restriction, and Prodrugs—Case History: An Example of a Conformational Restriction Approach, Med. Chem: Principle + Practice, 1994, 206-209, Chapter 14.

Gennaro, Alfonso, Remington: The Science and Practice of Pharmacy, 1995, 282-291, 1.

Ghinet, Alina et al, Studies on Pyrrolidinones. On the Application of Copper-Catalyzed Arylation of Methyl Pyroglutamate to Obtain a New Benzo[de]quinoline Scaffold, Tetrahedron, 2010, 215-221, 66.

International Search Report & Written Opinion dated Dec. 15, 2015 for PCT/US15/53865 filed Oct. 2, 2015 in the name of Allergan, Inc.

International Search Report and Written Opinion dated Feb. 27, 2015 for PCT/US13/56418 filed Aug. 23, 2010 in the name of Allergan, Inc.

International Search Report and Written Opinion dated Oct. 29, 2015 for PCT/US2015/16660 filed Feb. 19, 2015 in the name of Allergan, Inc.

Palacios, Francisco et al, Efficient Synthesis of 1-Azadienes Derived From α-Aminoesters. Regioselective Preparation of α-Dehydroamino Acids, Vinylglycines, and α-Amino Acids, Journal of Organic Chemistry, Sep. 2006, 7690-7696, 71(20).

* cited by examiner

ESTER PRODRUGS OF GAMMA-LACTAMS AND THEIR USE

CROSS-REFERENCE TO RELATED APPLICATIONS

This application is a national stage application of international application PCT/US2015/053865 filed on Oct. 2, 2015, which in turn claims the benefit of U.S. Provisional Application 62/058,802 filed on Oct. 2, 2014, which is incorporated by reference herein in its entirety and which serves as the basis for a priority and/or benefit claim of the present application.

FIELD

The present invention is directed to ester prodrugs of gamma-lactam compounds and methods of use of such compounds for the treatment of ocular diseases including, among other things, glaucoma and macular degeneration.

BACKGROUND

Glaucoma is a leading cause of blindness in the world. Indeed, over 2.5 million people in the United States suffer from the disease, and millions more are at risk of developing glaucoma. As the population ages, the number of individuals suffering from glaucoma will continue to grow since the elderly are being affected disproportionally.

Based on the etiology of glaucoma, it can be classified into primary and secondary glaucoma. Primary glaucoma, also known as congenital glaucoma, can occur in the absence of other ocular conditions, and its underlying causes are not known. It is known, however, that increased intraocular pressure (IOP) observed in primary glaucoma is due to the obstruction of aqueous humor flow out of the eye. Secondary glaucoma results from another pre-existing ocular disease such as uveitis, intraocular tumor, enlarged cataract, central retinal vein occlusion, trauma to the eye, operative procedures and intraocular hemorrhage. Generally, any interference with the outward flow of aqueous humor from the posterior chamber into the anterior chamber and subsequently into the canal of Schlemm can lead to secondary glaucoma.

Current treatments for glaucoma aim to reduce the pressure in the eye by decreasing the amount of aqueous fluid being produced or alternatively by enhancing the flow of fluid out of the eye by using mechanical means. Agents for topical application used to treat glaucoma include miotics (e.g., Isopto® Carpine, Ocusert®, Pilocar®, and Pilopine®) and epinephrines (e.g., Epifrin® and Propine®), which increase the outflow of fluid; beta blockers (e.g., Betagan®, Betimol®, Betoptic®, Ocupress®, Timoptic®, Optipranalol®); carbonic anhydrase inhibitors and alpha andrenergic agonists (e.g., Alphagan®, Iopidine®, Trusopt®), which reduce the amount of fluid; and prostaglandin analogs (e.g. Lumigan®, Rescula®, Travatan®, Xalatan®), which increase the outflow of fluid through a secondary drainage route.

The topical application of ophthalmic compositions for the treatment of glaucoma requires penetration of the drug through the cornea and into the anterior chamber, which contains aqueous humor, which then drains into the conventional outflow pathway. Intraoccular pressure is lowered by drugs acting in the Schlemm's canal and the uveal-scleral pathway. Penetration of the drug through the cornea requires a balance of hydrophobic and hydrophilic characteristics. In order to diffuse into the cornea the drug must be sufficiently soluble in non-polar media, and it must be sufficiently soluble in aqueous media in order to diffuse out of the cornea into the aqueous humor.

Potentially useful drugs for the treatment of glaucoma can be delivered as prodrug esters. The use of prodrug esters, which are cleaved enzymatically (e.g., in the cornea) to regenerate the active compound, can enhance penetration of the drug through the cornea into the anterior chamber. However, many esters are too hydrophobic to diffuse out of the relatively non-polar external layer of the cornea into the aqueous humor. Furthermore, such compounds are often not sufficiently soluble to formulate in aqueous solutions. Accordingly, there is a need in the art for ophthalmic compositions having the capability to penetrate through the cornea into the anterior chamber. At the same time such compositions need to exhibit sufficient hydrophilic properties to formulate in aqueous solution and to be soluble in the anterior chamber. Provided herein are compositions and methods addressing these and other needs in the art.

SUMMARY

In a first aspect, there is provided a compound having the structure of Formula (I):

(I)

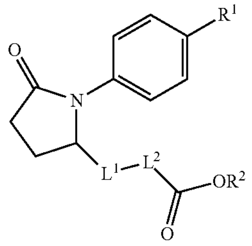

or pharmaceutically acceptable salt thereof. Regarding Formula (I), $R^1$ is substituted or unsubstituted $C_1$-$C_{10}$ alkyl or substituted or unsubstituted 2 to 10 membered heteroalkyl. $L^1$ is a bond, substituted or unsubstituted $C_1$-$C_{10}$ alkylene, or substituted or unsubstituted 2 to 10 membered heteroalkylene. $L^2$ is a bond, substituted or unsubstituted $C_1$-$C_{10}$ alkylene, substituted or unsubstituted arylene, or substituted or unsubstituted heteroarylene. $R^2$ is substituted or unsubstituted alkyl, substituted or unsubstituted heteroalkyl, substituted or unsubstituted cycloalkyl, substituted or unsubstituted hetercycloalkyl, substituted or unsubstituted aryl, or substituted or unsubstituted heteroaryl.

In another aspect, there is provided an ophthalmic pharmaceutical composition which includes a compound of Formula (I) as disclosed herein and an ophthalmically acceptable pharmaceutical excipient.

In another aspect, there is provided method for treating an ophthalmic disease in a subject. In some embodiments, the subject is a human. The method includes administering a therapeutically effective amount of a compound disclosed herein to a subject in need thereof.

In another aspect, there is provided a method for reducing corneal thickening, said method comprising administering a therapeutically effective amount of a compound as described herein to a subject in need thereof.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

Where substituents are specified as a range, the range encompasses each individual integer value of substituent including the beginning and ending value of the range. For example, the description of a substituent as "$C_1$ to $C_6$ alkyl" (or "$C_1$-$C_6$ alkyl" or "$C_{1-6}$ alkyl") encompasses $C_1$ alkyl, $C_2$ alkyl, $C_3$ alkyl, $C_4$ alkyl, $C_5$ alkyl, and $C_6$ alkyl. Similarly, the description of a value of "n" (e.g. "$(CH_2)_n$") as being "0 to 3" (or "0-3") encompasses values of "n" of 0, 1, 2, and 3. A skilled person will realize upon a reading of the present disclosure that similar considerations apply to other substituents that can be described in terms of a range (e.g. "5 to 10 ring atoms" and "1 to 3 rings").

The term "alkyl," by itself or as part of another substituent, means, unless otherwise stated, a straight (i.e., unbranched) or branched chain, or combination thereof, which may be fully saturated (referred to herein as a "saturated alkyl"), monounsaturated or polyunsaturated and can include di- and multivalent radicals, having the number of carbon atoms designated (i.e., $C_1$-$C_{10}$ means one to ten carbons). In some embodiments, all alkyls set forth as a substituent of the compounds provided herein are saturated alkyls. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. An "alkoxy" is an alkyl attached to the remainder of the molecule via an oxygen linker (—O—). An "alkylthio" is an alkyl attached to the remainder of the molecule via an sulfur linker (—S—). A "haloalkoxy" is an alkoxy substituted with a halogen. When the halogen is a fluoro, it is referred to herein as a "fluoroalkoxy." The term "alkyl" includes saturated alkyl, alkenyl and alkynyl. A saturated alkyl may have from 1 to 10 or 1 to 6 carbon atoms. The term "alkenyl" by itself or as part of another substituent, means, unless otherwise stated, a straight (i.e., unbranched) or branched hydrocarbon chain (e.g., two to ten, or two to six carbon atoms) having one or more double bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), and the like. The term "alkynyl" by itself or as part of another substituent, means, unless otherwise stated, a straight (i.e., unbranched) or branched hydrocarbon chain (e.g., two to ten or two to six carbon atoms) having one or more triple bonds. Examples of alkynyl groups include, but are not limited to, ethynyl, 1- and 3-propynyl, 3-butynyl, and the like.

The term "alkylene", "alkenylene, and "alkynylene" by itself or as part of another substituent means a divalent radical derived from an alkyl, alkenyl, or alkynyl as exemplified, but not limited, by methylene, ethylene, $—CH_2CH_2CH_2CH_2—$, vinylene and the like.

The term "amino" as used herein means a $—NH_2$. The term "carboxy" as used herein means —COOH (including pharmaceutically acceptable salts thereof).

The term "heteroalkyl," by itself or in combination with another term, means, unless otherwise stated, a stable straight or branched chain or combinations thereof, consisting of at least one carbon atom and at least one heteroatom selected from the group consisting of O, N, P, Si or S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2—S(O)—CH_3$, $—CH_2—CH_2—S(O)_2—CH_3$, $—CH{=}CH—O—CH_3$, $—Si(CH_3)_3$, $—CH_2—CH{=}N—O$ $CH_3$, $—CH{=}CH—N(CH_3)—CH_3$, $—O—CH_3$, $—O—CH_2—CH_3$, and —CN. Up to two heteroatoms may be consecutive, such as, for example, $—CH_2—NH—OCH_3$. Similarly, the term "heteroalkylene" by itself or as part of another substituent means a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). As described above, heteroalkyl groups, as used herein, include those groups that are attached to the remainder of the molecule through a heteroatom The terms "cycloalkyl" and "heterocycloalkyl," by themselves or in combination with other terms, represent, unless otherwise stated, non-aromatic cyclic versions of "alkyl" and "heteroalkyl", respectively (e.g., having 4 to 8 ring atoms). Additionally, for heterocycloalkyl, a heteroatom can occupy the position at which the heterocycle is attached to the remainder of the molecule. Heterocycloalkyls may include one or two ring heteroatoms selected from N, O, or $S(O)_{n'}$, where n' is an integer from 0 to 2, the remaining ring atoms being carbon. The heterocycloalkyl or cycloalkyl ring is optionally fused to one or more aryl or heteroaryl rings as defined herein (e.g., where the aryl and heteroaryl rings are monocyclic). The heterocycloalkyl or cycloalkyl ring fused to monocyclic aryl or heteroaryl ring may be referred to in this application as "bicyclic heterocycloalkyl" ring or a "bicyclic cycloalkyl" ring. Additionally, one or two ring carbon atoms in the heterocycloalkyl ring can optionally be replaced by a —CO— group. More specifically the term heterocycloalkyl includes, but is not limited to, pyrrolidino, piperidino, homopiperidino, 2-oxopyrrolidinyl, 2-oxopiperidinyl, morpholino, piperazino, tetrahydropyranyl, thiomorpholino, dihydroindolyl, and the like. When the heterocycloalkyl ring is unsaturated it can contain one or two ring double bonds provided that the ring is not aromatic. When the heterocycloalkyl group contains at least one nitrogen atom, it may also be referred to herein as heterocycloamino and is a subset of the heterocycloalkyl group. When the heterocycloalkyl group is a saturated ring and is not fused to aryl or heteroaryl ring as stated above, it may be referred to herein as a saturated monocyclic heterocycloalkyl. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, fluoromethyl, difluoromethyl, trifluoromethyl, 2,2,2-trifluoroethyl, 4-chlorobutyl, 3-bromopropyl, and the like.

The term "acyl" means —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl or substituted or unsubstituted heteroaryl.

The term "aryl" means, unless otherwise stated, an aromatic substituent which can be a single ring or multiple rings (preferably from 1 to 3 rings) which may be fused together (i.e., a fused ring aryl) or linked covalently. A fused ring aryl refers to multiple rings fused together wherein at least one of the fused rings is an aryl ring (e.g., phenyl, 1-naphthyl, 2-naphthyl, or 4-biphenyl). The term "heteroaryl" refers to aryl groups (or rings) that contain one or more (e.g., 4) heteroatoms selected from N, O, and S, wherein the nitrogen and sulfur atoms are optionally oxidized, and the nitrogen atom(s) are optionally quaternized, the remaining ring atoms being carbon. The heteroaryl may be a monovalent monocyclic, bicyclic, or tricyclic (e.g., monocyclic or bicyclic) aromatic radical of 5 to 14 (e.g., 5 to 10) ring atoms where one or more, (e.g., one, two, or three or four) ring atoms are heteroatom selected from N, O, or S. Examples include, but are not limited to, thienyl, isoindolyl, benzoxazolyl, pyridazinyl, triazolyl, tetrazolyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, 2-benzimidazolyl, 5-indolyl, 1-isoquinolyl, 5-isoquinolyl, 2-quinoxalinyl, 5-quinoxalinyl, 3-quinolyl, and 6-quinolyl. Thus, the term "heteroaryl" includes fused ring heteroaryl groups (i.e., multiple rings fused together wherein at least one of the fused rings is a heteroaromatic ring). A 5,6-fused ring heteroaryl refers to two rings fused together, wherein one ring has 5 members and the other ring has 6 members, and wherein at least one ring is a heteroaryl ring. Likewise, a 6,6-fused ring heteroaryl refers to two rings fused together, wherein one ring has 6 members and the other ring has 6 members, and wherein at least one ring is a heteroaryl ring. And a 6,5-fused ring heteroaryl refers to two rings fused together, wherein one ring has 6 members and the other ring has 5 members, and wherein at least one ring is a heteroaryl ring. A heteroaryl group can be attached to the remainder of the molecule through a carbon or heteroatom. An "arylene" and a "heteroarylene," alone or as part of another substituent means a divalent radical derived from an aryl and heteroaryl, respectively.

The terms "arylalkyl" and "heteroarylalkyl" is meant to include those radicals in which an aryl group or a heteroaryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom. The term "carbonyl" as used herein refers to a —C(O)— group.

The symbol "〰" indicates, as customary in the art, the point of attachment of a substituent.

"Optional" or "optionally" means that the subsequently described event or circumstance may but need not occur, and that the description includes instances where the event or circumstance occurs and instances in which it does not. For example, "heterocycloalkyl group optionally substituted with an alkyl group" means that the alkyl may but need not be present, and the description includes situations where the heterocycloalkyl group is substituted with an alkyl group and situations where the heterocycloalkyl group is not substituted with alkyl.

The term "alkylsulfonyl" as used herein means a moiety having the formula —S($O_2$)—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl" and "heteroaryl") are meant to include both substituted and unsubstituted forms of the indicated radical unless stated otherwise.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR'—C(NR'R"R'")=NR"", —NR—C(NR' R")=NR"", —S(O)R', —S(O)$_2$R', —S(O)$_2$NR'R", —NR$SO_2$R', —CN and —$NO_2$ in a number ranging from zero to (2m'+1), where m' is the total number of carbon atoms in such radical. R', R", R'" and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and may be selected from, for example: halogen, —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR'R", —NR"C(O)$_2$R', R', —NR—C(NR'R"R'")=NR"", —NR'—C(NR'R")=NR'", —S(O)R', —S(O)$_2$R', —S(O)$_2$NR'R", —NR'$SO_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R'', R''' and R'''' groups when more than one of these groups is present.

Two of the substituents on adjacent atoms of the aryl or heteroaryl ring may optionally form a ring of the formula $-T-C(O)-(CRR')_q-U-$, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula $-A-(CH_2)_r-B-$, wherein A and B are independently —CRR'—, —O—, —NR—, —S—, —S(O)—, $-S(O)_2-$, $-S(O)_2NR'-$ or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $-(CRR')_s-X'-(C''R''')_d-$, where s and d are independently integers of from 0 to 3, and X' is —O—, —NR'—, —S—, —S(O)—, $-S(O)_2-$, or $-S(O)_2NR'-$. The substituents R, R', R'' and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

Unless otherwise stated, the term “heteroatom” or “ring heteroatom” is meant to include oxygen (O), nitrogen (N), sulfur (S), phosphorus (P), and silicon (Si).

A “substituent group,” as used herein, means a group selected from the following moieties:

(A) —OH, $-NH_2$, —SH, —CN, $-CF_3$, $-NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, $-NH_2$, —SH, —CN, $-CF_3$, $-NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, $-NH_2$, —SH, —CN, $-CF_3$, $-NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, $-NH_2$, —SH, —CN, $-CF_3$, $-NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A “size-limited substituent” or “size-limited substituent group,” as used herein means a group selected from all of the substituents described above for a “substituent group,” wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A “lower substituent” or “lower substituent group,” as used herein means a group selected from all of the substituents described above for a “substituent group,” wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

Unless otherwise stated, structures depicted herein are also meant to include all stereochemical forms of the structure; e.g., the R and S configurations for each asymmetric center as well as cis and trans configurations. Therefore, single stereochemical isomers as well as enantiomeric and diastereomeric mixtures of the present compounds are within the scope of the invention.

The compounds of the present invention may have asymmetric centers and/or geometric isomers. Compounds of the present invention containing an asymmetrically substituted atom may be isolated in optically active or racemic forms. It is well known in the art how to prepare optically active forms, such as by resolution of materials. All chiral, diastereomeric, racemic forms are within the scope of this invention, unless the specific stereochemistry or isomeric form is specifically indicated. All possible tautomers and cis and trans isomers, as individual forms and mixtures thereof are within the scope of this invention. Additionally, as used herein the term alkyl includes all the possible isomeric forms of the alkyl group albeit only a few examples are set forth. Furthermore, when the cyclic groups such as aryl, heteroaryl, heterocycloalkyl are substituted, they include all the positional isomers albeit only a few examples are set forth. Furthermore, all polymorphic forms, including amorphous form, and hydrates of a compound disclosed herein are within the scope of this invention.

Certain compounds of the present invention possess asymmetric carbon atoms (optical centers) or double bonds; the racemates, diastereomers, tautomers, geometric isomers and individual isomers are encompassed within the scope of the present invention, as are enantiomers. The compounds of the present invention do not include those which are known in the art to be too unstable to synthesize and/or isolate.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

The terms “a,” “an,” or “a(n),” when used in reference to a group of substituents herein, mean at least one. For example, where a compound is substituted with “an” alkyl or aryl, the compound is optionally substituted with at least one alkyl and/or at least one aryl.

Unless indicated otherwise, the term "derivative" in the context of a compound disclosed herein refers to a compound afforded by chemical modification, e.g., by the bonding of one or more substituent groups as described herein.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{1A}$-substituted or unsubstituted alkyl, a plurality of $R^{1A}$ substituents may be attached to the alkyl moiety wherein each $R^{1A}$ substituent is optionally different. Where an R-substituted moiety is substituted with a plurality R substituents, each of the R-substituents may be differentiated herein using a prime symbol (') such as R', R", etc. For example, where a moiety is $R^{1A}$-substituted or unsubstituted alkyl, and the moiety is substituted with a plurality of $R^{1A}$ substituents, the plurality of $R^{1A}$ substituents may be differentiated as $R^{1A'}$, $R^{1A''}$, $R^{1A'''}$, etc. In some embodiments, the plurality of R substituents is 3. In some embodiments, the plurality of R substituents is 2.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like. See e.g., Berge et al., "Pharmaceutical Salts", *Journal of Pharmaceutical Science,* 1977, 66, 1-19). Additional information on suitable pharmaceutically acceptable salts can be found in REMINGTON'S PHARMACEUTICAL SCIENCES, 17th ed., Mack Publishing Company, Easton, Pa., 1985, which is incorporated herein by reference. Certain specific compounds of the present invention contain both basic and acidic functionalities that allow the compounds to be converted into either base or acid addition salts.

Thus, in some embodiments, the compounds disclosed herein can exist as salts. Examples of such salts include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts can be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

The term "prodrug" is used according to its plain ordinary meaning and is intended to mean compounds that require a chemical or enzymatic transformation in order to release the active parent drug in vivo prior to producing a pharmacological effect. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

A "pharmaceutically acceptable carrier" or "pharmaceutically acceptable excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. An "ophthalmically pharmaceutically acceptable excipient" refers to a pharmaceutically acceptable excipient that is generally safe, non-toxic and neither biologically nor otherwise undesirable for veterinary ophthalmic use and human ophthalmic use. An "ophthalmic pharmaceutical composition" refers to a pharmaceutical composition that is generally safe, non-toxic and neither biologically nor otherwise undesirable for veterinary ophthalmic use and human ophthalmic use.

The terms "treating" or "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating, and/or improving a patient's physical or mental well-being. The treatment or amelioration of symptoms can be based on objective or subjective parameters; including the results of a physical examination. For example, the certain methods presented herein can successfully treat glaucoma by decreasing the intraocular pressure.

An "effective amount" of a compound is an amount sufficient to contribute to the treatment, prevention (e.g. prophylaxis), and/or reduction of a symptom or symptoms of a disease (e.g. glaucoma, elevated intraocular pressure, corneal thickening, and/or others identifiable to a skilled person upon a reading of the present disclosure). Where recited in reference to a disease treatment, an "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of a disease, disorder or condition, or reducing the likelihood of the onset (or reoccurrence) of a disease, disorder or condition or symptoms thereof. The full prophylactic effect does not necessarily occur by administration of one dose, and may occur only after administration of a series of doses. In one embodiment, a prophylactically effective amount is administered in one or more administrations.

The term "topical" in the context of methods described herein relates in the customary sense to the administration of a compound or pharmaceutical composition which is incorporated into a suitable pharmaceutical carrier and administered at a topical treatment site of a subject. Accordingly, the term "topical pharmaceutical composition" includes those pharmaceutical forms in which the compound is administered externally by direct contact with a topical treatment site, e.g., the eye or the skin. The term "topical ocular pharmaceutical composition" refers to a pharmaceutical composition suitable for administering directly to the eye. The term "topical epidermal pharmaceutical composition" refers to a pharmaceutical composition suitable for administering directed to the epidermal layer of the skin, e.g., the palpebra, the supercilium, the scalp, or the body. The term "topical administering" refers to administering externally by direct contact with a topical treatment site. The term "topical epidermal administering" refers to administering externally by direct contact with the epidermis. The term "topical ocular administering" refers to administering externally by direct contact with the eye.

II. Compounds

In a first aspect, there is provided a compound having the structure of Formula (I):

(I)

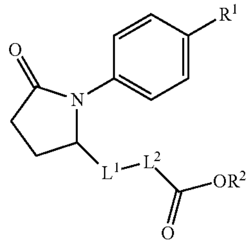

or pharmaceutically acceptable salt thereof. Regarding Formula (I), $R^1$ is substituted or unsubstituted $C_1$-$C_{10}$ alkyl or substituted or unsubstituted 2 to 10 membered heteroalkyl. $L^1$ is a bond, substituted or unsubstituted $C_1$-$C_{10}$ alkylene, or substituted or unsubstituted 2 to 10 membered heteroalkylene. $L^2$ is a bond, substituted or unsubstituted $C_1$-$C_{10}$ alkylene, substituted or unsubstituted arylene, or substituted or unsubstituted heteroarylene. $R^2$ is substituted or unsubstituted alkyl, substituted or unsubstituted heteroalkyl, substituted or unsubstituted cycloalkyl, substituted or unsubstituted hetercycloalkyl, substituted or unsubstituted aryl, or substituted or unsubstituted heteroaryl. In one embodiment, $R^2$ is not hydroxyethyl.

In one embodiment, $R^1$ is substituted or unsubstituted $C_1$-$C_{10}$ alkyl, or substituted or unsubstituted 2 to 10 membered heteroalkyl, wherein "substituted" groups are substituted by $R^{1A}$, and $R^{1A}$ is hydroxyl or halogen. It is understood that if a functionality (e.g., "$C_1$-$C_{10}$ alkyl") is substituted (e.g., "$C_1$-$C_{10}$ alkyl substituted by . . . ") then substitution can be a single substitution or multiple substitutions (i.e., a "plural substitution") wherein each substituent is selected independently from any other substituent. For example, the term "$C_1$-$C_{10}$ alkyl substituted by $R^{1A}$" in the context of a formula disclosed herein refers to $C_1$-$C_{10}$ alkyl having i) a single substituent $R^{1A}$, or b) a plurality of substituents with a plurality of substituents $R^{1A}$, wherein $R^{1A}$ at each occurrence is independently selected.

In one embodiment, $R^1$ is unsubstituted $C_1$-$C_{10}$ alkyl or unsubstituted 2 to 10 membered heteroalkyl. In one embodiment, $R^1$ is unsubstituted $C_1$, $C_2$, $C_3$, $C_4$, $C_5$, $C_6$, $C_7$, $C_8$, $C_9$, or $C_{10}$ alkyl. In one embodiment, $R^1$ is unsubstituted 2 to 10 membered heteroalkyl, e.g., 2, 3, 4, 5, 6, 7, 8, 9 or 10 membered heteroalkyl.

In one embodiment, $R^1$ is unsubstituted $C_1$-$C_{10}$ alkyl or $C_1$-$C_{10}$ alkyl substituted by $R^{1A}$. In one embodiment, $C_1$-$C_{10}$ alkyl is $C_1$, $C_2$, $C_3$, $C_4$, $C_5$, $C_6$, $C_7$, $C_8$, $C_9$, or $C_{10}$ alkyl. In one embodiment, $R^1$ is $C_1$-$C_{10}$ alkyl substituted by $R^{1A}$. In one embodiment, $R^1$ $C_6$ alkyl substituted by $R^{1A}$. In one embodiment, $R^1$ is hydroxyl-substituted $C_6$ alkyl.

In one embodiment, $R^1$ is unsubstituted 2 to 10 membered heteroalkyl or 2 to 10 membered heteroalkyl substituted by $R^{1A}$. In one embodiment, $R^{1A}$ is hydroxyl or halogen. In one embodiment, $R^{1A}$ is hydroxyl. In one embodiment, $R^{1A}$ is halogen. In one embodiment, $R^{1A}$ is fluoro.

In one embodiment, $L^1$ is substituted or unsubstituted $C_1$-$C_6$ alkylene. In one embodiment, $L^1$ is unsubstituted $C_1$-$C_6$ alkylene. In one embodiment, $L^1$ is unsubstituted $C_1$, $C_2$, $C_3$, $C_4$, $C_5$, or $C_6$ alkylene. In one embodiment, $L^1$ is substituted or unsubstituted propylene. In one embodiment, $L^1$ is $C_1$-$C_{10}$ alkylene substituted by $L^{1A}$, or 2 to 10 membered heteroalkylene substituted by $L^{1A}$, wherein $L^{1A}$ at each occurrence is independently halogen or hydroxyl. In one embodiment, $L^{1A}$ is fluoro. In one embodiment, $L^1$ is unsubstituted $C_1$-$C_{10}$ alkylene or $C_1$-$C_{10}$ alkylene substituted by $L^{1A}$, wherein $L^{1A}$ at each occurrence is independently is hydroxyl or halogen. In one embodiment, $L^{1A}$ is hydroxyl. In one embodiment, $L^{1A}$ is halogen. In one embodiment, $L^{1A}$ is fluoro. In one embodiment, $L^1$ is $C_2$-$C_6$ alkylene substituted by $L^{1A}$ and $L^{1A}$ is halogen. In one embodiment, $L^1$ is $C_2$-$C_6$ alkylene substituted by $L^{1A}$ and $L^{1A}$ is fluoro. In one embodiment, $L^1$ is unsubstituted $C_2$-$C_6$ alkylene. In one embodiment, $L^1$ is unsubstituted propylene.

In one embodiment, $L^2$ is substituted or unsubstituted alkylene, substituted or unsubstituted arylene or substituted or unsubstituted heteroarylene. In one embodiment, $L^2$ is unsubstituted $C_1$-$C_{10}$ alkylene, $C_1$-$C_{10}$ alkylene substituted by $L^{2A}$, arylene substituted by $L^{2A}$, or heteroarylene substituted by $L^{2A}$, wherein $L^{2A}$ is hydroxyl or halogen. In one embodiment, $L^2$ is heteroarylene substituted by $L^{2A}$. In one embodiment, $L^2$ is unsubstituted heteroarylene. In one embodiment, $L^2$ is unsubstituted $C_1$-$C_{10}$ alkylene. In one embodiment, $L^2$ is $C_1$-$C_{10}$ alkylene substituted by $L^{2A}$. In one embodiment, $L^2$ is unsubstituted arylene, unsubstituted heteroarylene or unsubstituted alkylene. In one embodiment, $L^2$ is unsubstituted arylene. In one embodiment, $L^2$ is unsubstituted alkylene.

In one embodiment, $L^2$ is unsubstituted pyridinylene, unsubstituted thiophenylene, unsubstituted pyrrolylene, or unsubstituted furanylene. The terms "pyridinylene," "thiophenylene," "pyrrolylene," "furanylene," and the like refer, as customary in the art, to divalent forms of pyridine, thiophene, pyrrole, and furan, respectively. A person of skill in the art will immediately recognize for example, that the terms "pyridinylene," "thiophenylene," "pyrrolylene" and "furanylene" are equivalent to pyridinediyl, thiophenediyl, pyrrolediyl and furnadiyl and the like.

In one embodiment, $R^2$ is substituted or unsubstituted $C_1$-$C_{10}$ alkyl, or substituted or unsubstituted 2 to 10 membered heteroalkyl. In one embodiment, $R^2$ is substituted or unsubstituted $C_1$-$C_{10}$ alkyl. In one embodiment, $R^2$ is substituted or unsubstituted 2 to 10 membered heteroalkyl.

In one embodiment, $R^2$ is unsubstituted $C_1$-$C_{10}$ alkyl, $C_1$-$C_{10}$ alkyl substituted by $R^{2A}$, unsubstituted 2 to 10 membered heteroalkyl, or 2 to 10 membered heteroalkyl substituted by $R^{2A}$. $R^{2A}$ at each occurrence is independently halogen, hydroxyl, unsubstituted alkyl, alkyl substituted by $R^{2B}$, unsubstituted heteroalkyl, heteroalky substituted by $R^{2B}$, unsubstituted cycloalkyl, cycloalkyl substituted by $R^{2B}$, unsubstituted heterocycloalkyl, heterocycloalkyl substituted by $R^{2B}$, unsubstituted aryl, aryl substituted by $R^{2B}$, unsubstituted heteroaryl, or heteroaryl substituted by $R^{2B}$. $R^{2B}$ at each occurrence is independently halogen, hydroxyl, unsubstituted alkyl, alkyl substituted by $R^{2C}$, unsubstituted heteroalkyl, heteroalky substituted by $R^{2C}$, unsubstituted cycloalkyl, cycloalkyl substituted by $R^{2C}$, unsubstituted heterocycloalkyl, heterocycloalkyl substituted by $R^{2C}$, unsubstituted aryl, aryl substituted by $R^{2C}$, unsubstituted heteroaryl, or heteroaryl substituted by $R^{2C}$. $R^{2C}$ at each occurrence is independently halogen, hydroxyl, unsubstituted alkyl, unsubstituted heteroalkyl, unsubstituted cycloalkyl, unsubstituted heterocycloalkyl, unsubstituted aryl or unsubstituted heteroaryl.

In one embodiment, $R^2$ is unsubstituted $C_1$-$C_{10}$ alkyl or $C_1$-$C_{10}$ alkyl substituted by $R^{2A}$. In one embodiment, $R^2$ is unsubstituted 2 to 10 membered heteroalkyl or 2 to 10 membered heteroalkyl substituted by $R^{2A}$.

In one embodiment, $R^{2A}$ is unsubstituted alkyl, alkyl substituted by $R^{2B}$, unsubstituted heteroalkyl, or heteroalkyl substituted by $R^{2B}$. In one embodiment, $R^{2A}$ is unsubstituted alkyl or alkyl substituted by $R^{2B}$. In one embodiment, $R^{2A}$ is unsubstituted heteroalkyl or heteroalkyl substituted by $R^{2B}$.

In one embodiment, $R^{2A}$ is halogen or hydroxyl. In one embodiment, $R^{2A}$ is halogen. In one embodiment, $R^{2A}$ is hydroxyl. In one embodiment, $R^{2A}$ is fluoro.

In one embodiment, $L^2$ is thiophene-2,5-diyl. In one embodiment, $L^1$ is propylene-1,3-diyl.

In one embodiment, $R^2$ is substituted with a single substituent $R^{2A}$ or a plurality of substituents $R^{2A}$, wherein $R^{2A}$ at each occurrence is independently selected. In one embodiment, $R^{2A}$ at each occurrence is halogen. In one embodiment, $R^{2A}$ at each occurrence is hydroxyl.

In one embodiment, there is provided a compound having the structure of Formula (II):

(II)

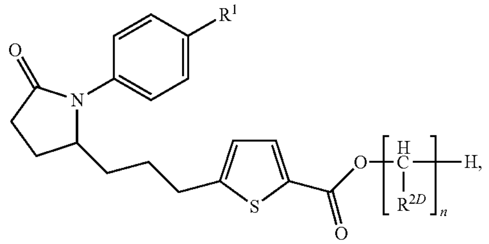

wherein n is 1 to 10, and $R^{2D}$ at each occurrence is independently hydrogen or hydroxyl. In one embodiment, n is 1, 2, 3, 4, 5, 6, 7, 8, 9 or 10. In one embodiment, 1, 2, 3, 4, 5 or 6 substituents $R^{2D}$ are not hydrogen. In one embodiment, 2 substituents $R^{2D}$ are not hydrogen. In one embodiment, 3 substituents $R^{2D}$ are not hydrogen. In one embodiment, 4 substituents $R^{2D}$ are not hydrogen. In one embodiment, 5 substituents $R^{2D}$ are not hydrogen. In one embodiment, 6 substituents $R^{2D}$ are not hydrogen. In one embodiment, 1 substituent $R^{2D}$ is hydroxyl. In one embodiment, 2 substituents $R^{2D}$ are hydroxyl. In one embodiment, 3 substituents $R^{2D}$ are hydroxyl. In one embodiment, 4 substituents $R^{2D}$ are hydroxyl. In one embodiment, n is greater than 1, e.g., 2, 3, 4, 5, 6, 7, 8, 9 or 10.

In one embodiment, there is provided a compound having the structure of Formula (III):

(III)

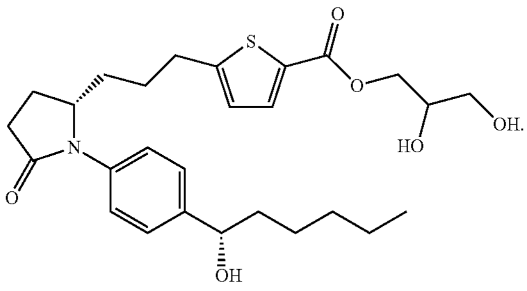

In one embodiment, there is provided a compound having the structure of Formula (IIIa), also referred to herein as compound 3:

(IIIa)

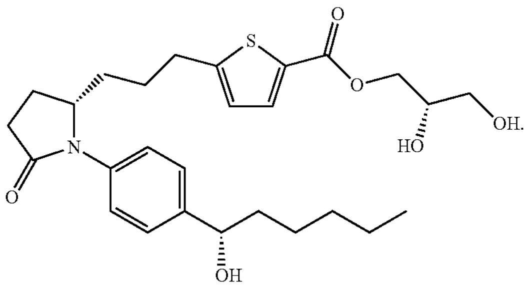 [SMILES: CCCCC[C@H](O)c1ccc(N2C(=O)CC[C@@H]2CCCc2ccc(C(=O)OC[C@@H](O)CO)s2)cc1]

In one embodiment, there is provided a compound having the structure of Formula (IIIb), also referred to herein as compound 5:

(IIIb)
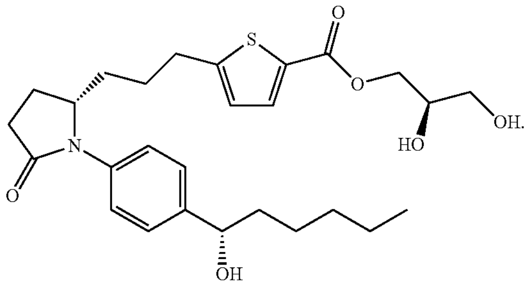
In one embodiment, there is provided a compound having the structure of Formula (IV):
(IV)
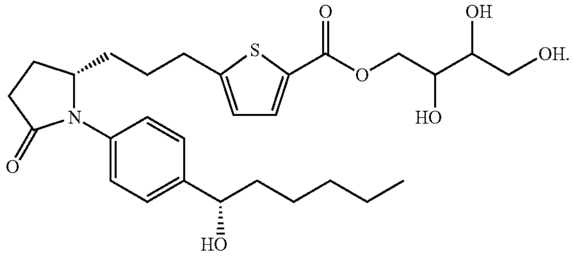
In one embodiment, the compound has the structure of one of Formulae:
(IVa)
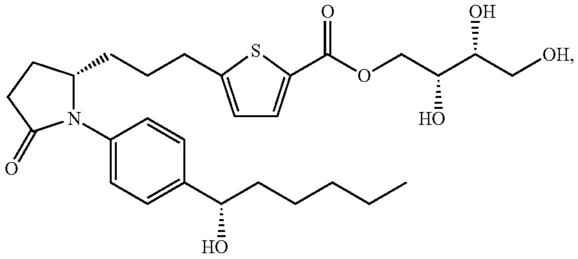
(IVb)
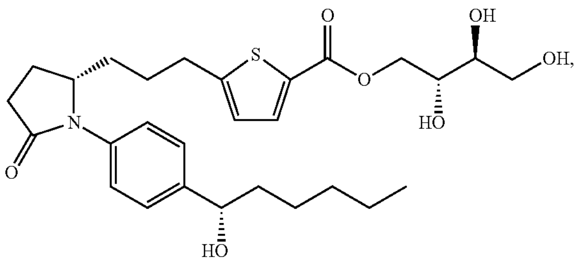
-continued
(IVc)
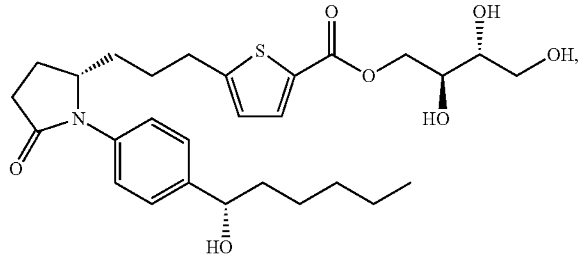
or
(IVd)
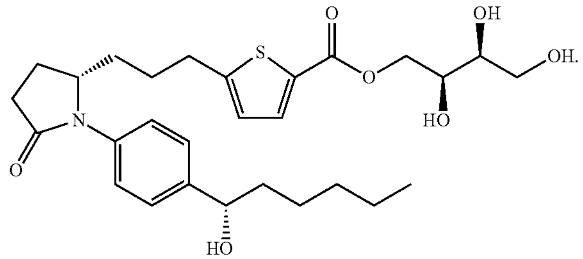
In one embodiment, there is provided a compound having the structure of Formula (V):
(V)
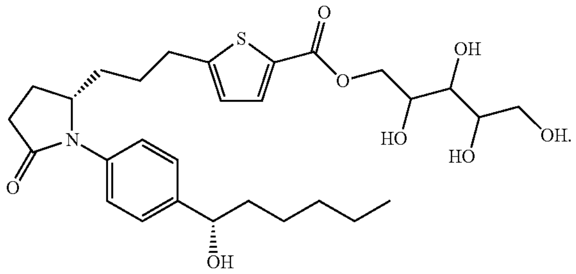
In one embodiment, the compound has the structure of one of Formulae
(Va)
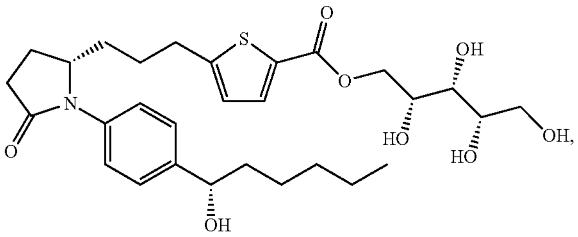

-continued
(Vb)
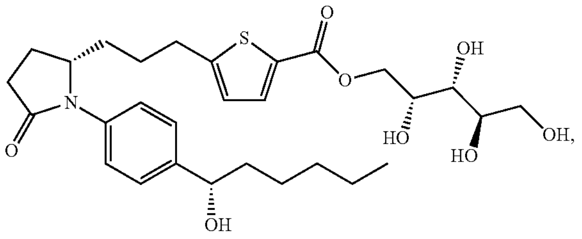
(Vc)
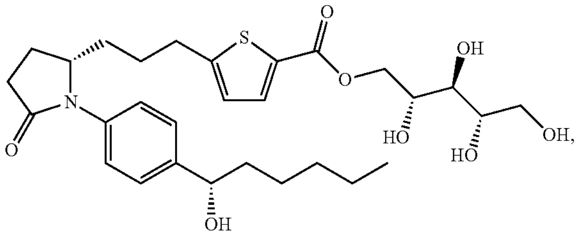
(Vd)
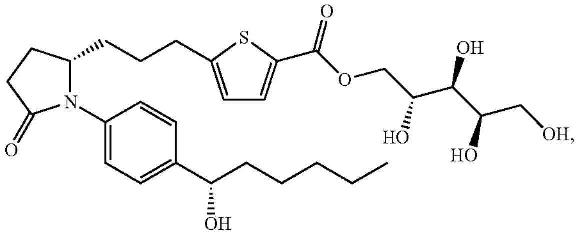
(Ve)
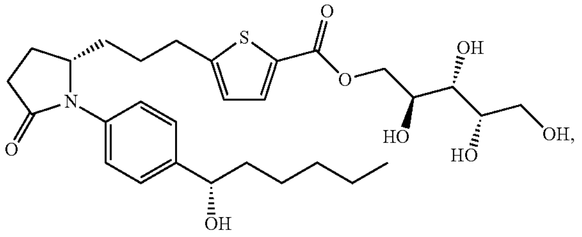
(Vf)
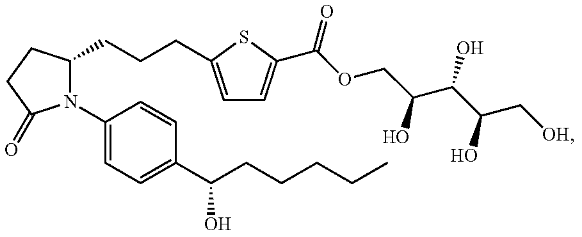
(Vg)
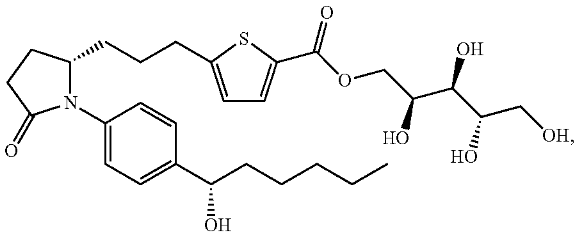
or
-continued
(Vh)
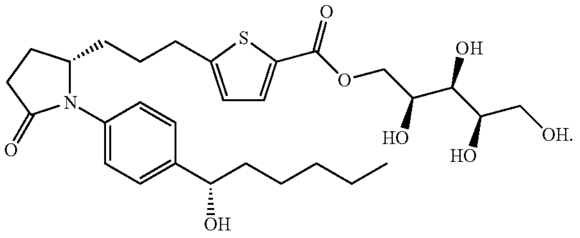
In one embodiment, there is provided a compound having the structure of Formula (VI):
(VI)
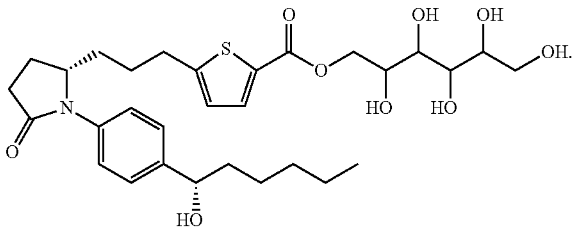
In one embodiment, the compound has the structure of one of Formulae
(VIa)
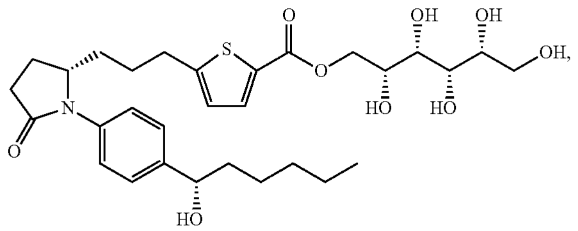
(VIb)
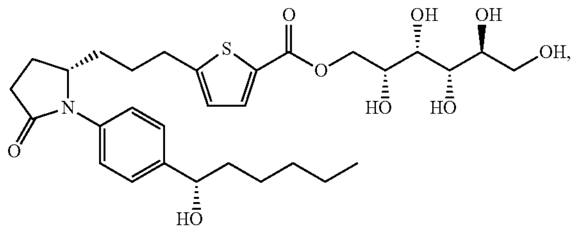
(VIc)
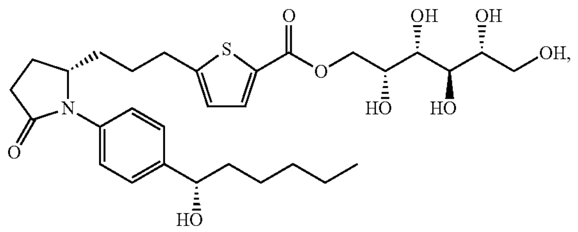

-continued
(VId)
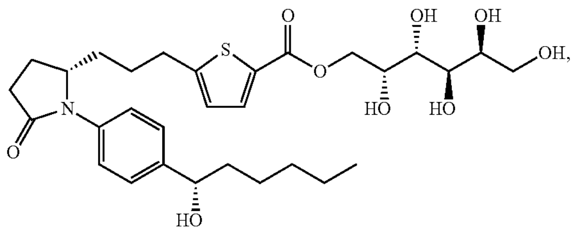
(VIe)
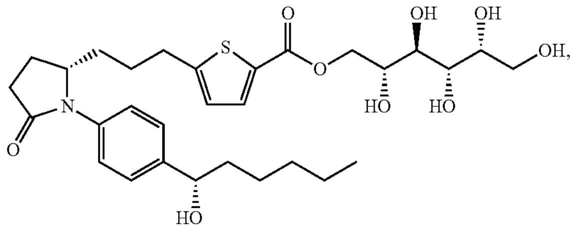
(VIf)
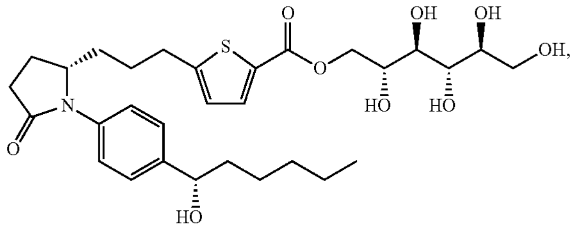
(VIg)
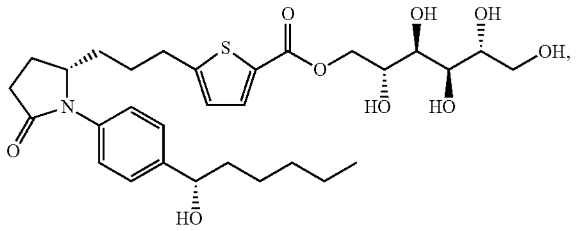
(VIh)
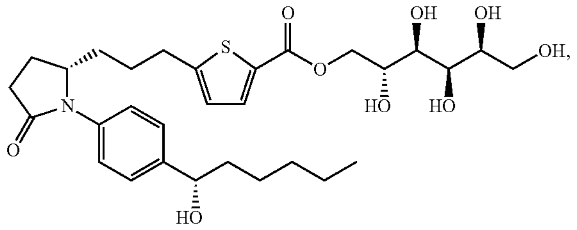
(VIi)
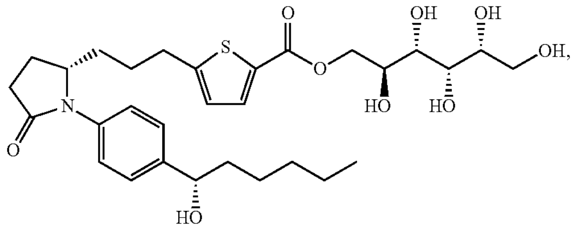
-continued
(VIj)
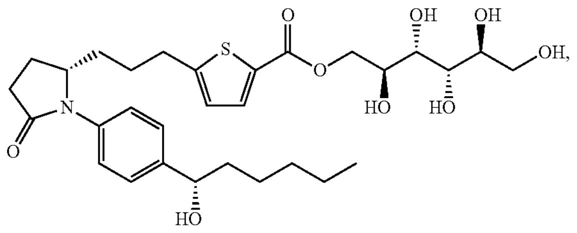
(VIk)
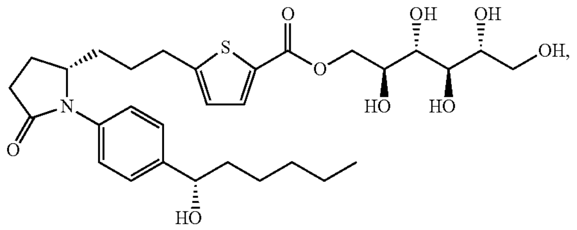
(VIl)
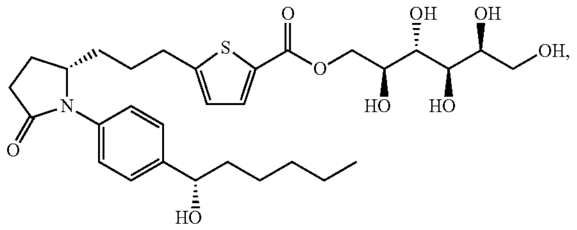
(VIm)
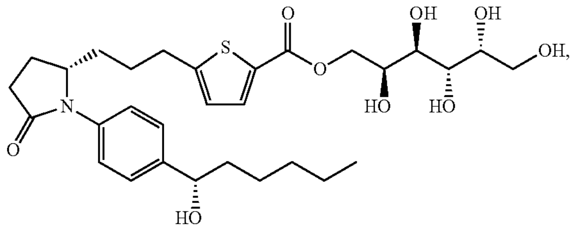
(VIn)
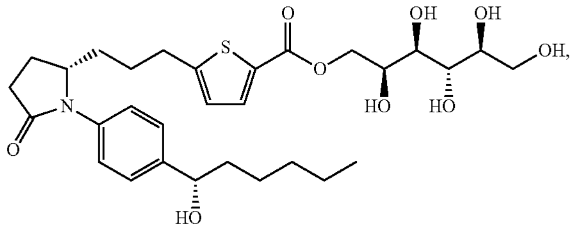
(VIo)
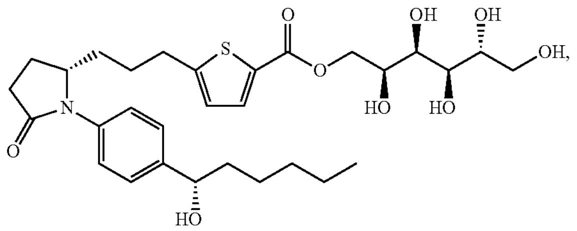
or -continued (VIp)

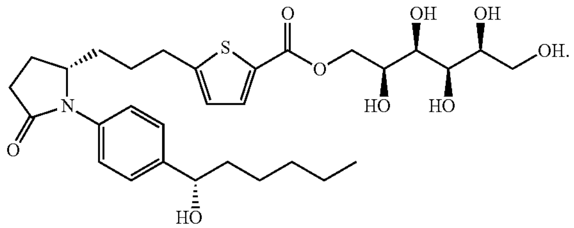

It is understood that a compound described herein, e.g., a compound with structure of any one of Formulae (I), (II), (III), (IV), (V), (VI) or derivative, isomer or enantiomer thereof, can be provided, where applicable, as a pharmaceutically acceptable salt as defined herein, where the compound admits to formation of a pharmaceutically acceptable salt. In one embodiment, there is provided a pharmaceutically acceptable salt of a compound with structure of any one of Formulae (I), (II), (III), (IV), (V), (VI), or isomer or enantiomer thereof, wherein the compound admits to formation of a pharmaceutically acceptable salt.

III. Pharmaceutical Compositions

In another aspect, there is provided an ophthalmic pharmaceutical composition including a ophthalmically pharmaceutically excipient and a compound provided herein (e.g., a compound with structure of Formula (I), (II), (III), (IV), (V), (VI), or derivative, isomer or enantiomer thereof and including embodiments thereof identifiable to a skilled person upon a reading of the present disclosure).

In one embodiment, the compound has the structure of Formulae (I). In one embodiment, the compound has the structure of Formulae (II). In one embodiment, the compound has the structure of Formulae (III). In one embodiment, the compound has the structure of one of Formulae (IIIa)-(IIIb). In one embodiment, the compound has the structure of Formulae (IV). In one embodiment, the compound has the structure of one of Formulae (IVa)-(IVd). In one embodiment, the compound has the structure of Formulae (V). In one embodiment, the compound has the structure of one of Formulae (Va)-(Vh). In one embodiment, the compound has the structure of Formulae (VI). In one embodiment, the compound has the structure of one of Formulae (VIa)-(VIp).

In one embodiment, the pharmaceutical composition is a solution, emulsion, gel or foam. In one embodiment, the pharmaceutical composition is a solution. In one embodiment, the pharmaceutical composition is an emulsion. In one embodiment, the pharmaceutical composition is a gel. In one embodiment, the pharmaceutical composition is a foam.

In some embodiments, when the compounds described herein (e.g. compounds of Formula (I), (II), (III), (IV), (V), or (VI)) are part of a composition, the compounds are the only active ingredients which result in the biological effects described herein (e.g., reduction of intraocular pressure and others identifiable to a skilled person upon a reading of the present disclosure). The term "active ingredient" as used herein refers to a component which is responsible for the biological effects described herein (e.g. treatment of glaucoma, elevated intraocular pressure, macular degeneration and others identifiable to a skilled person upon a reading of the present disclosure), whereas the other components of the composition (e.g. excipients, carriers, and diluents) are not responsible for the biological effects, even if they have other functions in the composition which are necessary or desired as part of the formulation (e.g., lubrication, flavoring, pH control, emulsification, and other functions other than the biological effects described herein).

A. Formulations

The compounds and pharmaceutical compositions disclosed herein can be prepared and administered in a variety of forms including solution, emulsion, gel or foam. Accordingly, pharmaceutical compositions contemplated herein include a pharmaceutically acceptable carrier or excipient and one or more compounds described herein. "Solution" refers in the customary sense to a liquid pharmaceutical composition in which a compound (e.g., a compound described herein), is at least partially dissolved, preferably fully dissolved, and which can be administered as a liquid. "Emulsion" refers in the customary sense to a mixture of two or more immiscible liquids, one compound (e.g., a compound described herein or solution thereof) being dispersed through the other compound (e.g., a carrier as described herein). "Gel" refers in the customary sense to a highly viscous solution, emulsion, or colloidal suspension of a compound within a continuous fluid phase resulting in a viscous semirigid fluid. "Colloid" refers in the customary sense to a composition which includes a continuous medium throughout which are distributed small particles which do not settle under the influence of gravity. "Foam" refers in the customary sense to a composition which includes a continuous medium (i.e., solution, emulsion, gel and the like) through which gas (e.g., air) is dispersed.

Pharmaceutical compositions contemplated herein may be prepared by combining a therapeutically effective amount of at least one compound as described herein as an active ingredient in combination with one or more conventional pharmaceutically acceptable excipients, and by preparation of unit dosage forms suitable for topical use. The therapeutically efficient amount typically is between about 0.0001 and about 5% (w/v), preferably about 0.001 to about 1.0% (w/v) in liquid formulations which include solutions, emulsions, gels and foams. Pharmaceutical admixtures suitable for use in the present invention include those described, for example, in PHARMACEUTICAL SCIENCES (17th Ed., Mack Pub. Co., Easton, Pa.) and WO 96/05309, the teachings of both of which are hereby incorporated by reference.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. US Patent application publication No. US 2011-0124736 A1, also corresponding to U.S. patent application Ser. No. 12/940,711, is hereby incorporated by reference in its entirety.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

An ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ophthalmic formulations of the present invention are conveniently packaged in forms suitable for metered application, such as in containers equipped with an orifice, to facilitate application to the eye. Vials suitable for unit dose application are usually made of suitable inert, non-toxic plastic material, and generally contain between about 0.5 and about 15 ml solution, emulsion, gel or foam. One package may contain one or more unit doses.

Preservative-free solutions are often formulated in non-resealable containers containing up to about ten, preferably up to about five units doses, where a typical unit dose is from one to about 8 drops, preferably one to about 3 drops.

Typically, the compounds are applied repeatedly for a sustained period of time topically on the part of the body to be treated, for example, the eye. The preferred dosage regimen will generally involve regular administration for a period of treatment of at least one month, more preferably at least three months, and most preferably at least six months. The regular administration can be 1, 2, 3, 4 or even more times per day.

IV. Methods of Treatment

Provided herein are methods of treating ophthalmic diseases and disorders in a subject or patient. In some embodiments the subject or patient is a mammal. In preferred embodiments, the subject or patient is a human. The methods include administering a therapeutically effective amount of a compound with structure of any one of Formulae (I)-(VI) to a subject in need thereof. In one embodiment, the method includes administering a therapeutically effective amount of a compound with structure of any one of Formulae (I)-(III) to a subject in need thereof. In one embodiment, the method includes administering a therapeutically effective amount of a compound with structure of any one of Formulae (I)-(VI) or derivative, isomer or enantiomer thereof, to a subject in need thereof.

In one embodiment, there is provided a method for treating glaucoma, including administering to a subject in need thereof an effective amount of a compound as described herein, or an ophthalmic pharmaceutical composition as described herein. In one embodiment, there is provided a method for treating ocular hypertension, including administering to a subject in need thereof an effective amount of a compound as described herein, or an ophthalmic pharmaceutical composition as described herein. In one embodiment, there is provided a method for treating macular degeneration, including administering to a subject in need thereof an effective amount of a compound as described herein, or an ophthalmic pharmaceutical composition as described herein. In one embodiment, the disease results from increased intraocular pressure. The term “increased intraocular pressure” refers, in the customary sense, to an intraocular pressure which is greater than that which would be as judged as normal by a practitioner in the medical arts. Without wishing to be bound by any theory, it is believed that increased intraocular pressure is associated with a variety of diseases, including, for example, glaucoma.

In one embodiment, there is provided a method of use of a compound disclosed herein for the manufacture of a medicament for an ophthalmic disease. In one embodiment, the compound has the structure of any one of Formulae I, II, III, IV, V or VI. In one embodiment, the compound has the structure of Formula I. In one embodiment, the compound has the structure of Formula II. In one embodiment, the compound has the structure of Formula III. In one embodiment, the compound has the structure of one of Formulae (IIIa)-(IIIb). In one embodiment, the compound has the structure of Formula IV. In one embodiment, the compound has the structure of one of Formulae (IVa)-(IVd). In one embodiment, the compound has the structure of Formula V. In one embodiment, the compound has the structure of one of Formulae (Va)-(Vh). In one embodiment, the compound has the structure of Formula VI. In one embodiment, the compound has the structure of one of Formulae (VIa)-(VIp).

In another aspect, there is provided a method for treating glaucoma or ocular hypertension, the method including administering to a subject in need thereof an effective amount of a compound as described herein, or a pharmaceutical composition as described herein, in combination with another drug useful for the treatment of glaucoma, ocular hypertension, or other condition.

In one embodiment, there is provided a combination treatment with a β-blocker (or β-adrenergic antagonist) including carteolol, levobunolol, metiparanolol, timolol hemihydrate, timolol maleate, β1-selective antagonists such as betaxolol, and the like, or pharmaceutically acceptable salts or prodrugs thereof.

In one embodiment, there is provided a combination treatment with an adrenergic agonists including non-selective adrenergic agonists such as epinephrine borate, epinephrine hydrochloride, and dipivefrin, and the like, or pharmaceutically acceptable salts or prodrugs thereof, and α2-selective adrenergic agonists such as apraclonidine, brimonidine, and the like, or pharmaceutically acceptable salts or prodrugs thereof.

In one embodiment, there is provided a combination treatment with a carbonic anhydrase inhibitors including acetazolamide, dichlorphenamide, methazolamide, brinzolamide, dorzolamide, and the like, or pharmaceutically acceptable salts or prodrugs thereof.

In one embodiment, there is provided a combination treatment with a cholinergic agonist including direct acting cholinergic agonists such as carbachol, pilocarpine hydrochloride, pilocarpine nitrate, pilocarpine, and the like, or pharmaceutically acceptable salts or prodrugs thereof.

In one embodiment, there is provided a combination treatment with a chlolinesterase inhibitors such as demecarium, echothiophate, physostigmine, and the like, or pharmaceutically acceptable salts or prodrugs thereof.

In one embodiment, there is provided a combination treatment with a glutamate antagonists or other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-1 01,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof.

In one embodiment, there is provided a combination treatment with a prostamides such as bimatoprost, or pharmaceutically acceptable salts or prodrugs thereof.

In one embodiment, there is provided a combination treatment with a prostaglandin including travoprost, UF0-21, chloprostenol, fluprostenol, 13,14-dihydro-chloprostenol, isopropyl unoprostone, latanoprost and the like.

In one embodiment, there is provided a combination treatment with a cannabinoid including CB1 agonists such as WIN-55212-2 and CP-55940 and the like, or pharmaceutically acceptable salts or prodrugs thereof.

Further to any embodiment disclosed above of a method of treating an ophthalmic disease, in one embodiment the administering is topical administering.

In another aspect, there is provided a method for reducing corneal thickening as known in the art. The method includes administering a therapeutically effective amount of a compound as described herein to a subject in need thereof. In one embodiment, the subject suffers from glaucoma. In one embodiment, the subject suffers from ocular hypertension.

Examples

Abbreviations used herein have the customary meaning in the chemical arts. Specific abbreviations include the following: TBDMS: tert-butyldimethylsilyl; DMF: N,N-dimethylformamide; EDC: N-[3-dimethylaminopropyl]-N'-ethylcarbodiimide hydrochloride; DMAP: 4-(dimethylamino) pyridine; THF: tetrahydrofuran; $Bu_4NF$: tetrabutylammonium fluoride; PPTS: pyridinium p-toluenesulfonate.

Example 1

(S)-2,3-dihydroxypropyl 5-(3-((S)-1-(4-((S)-1-hydroxyhexyl)phenyl)-5-oxopyrrolidin-2-yl)propyl) thiophene-2-carboxylate (3)

An exemplary synthesis of compound 3 is set forth in Scheme 1 following.

Scheme 1

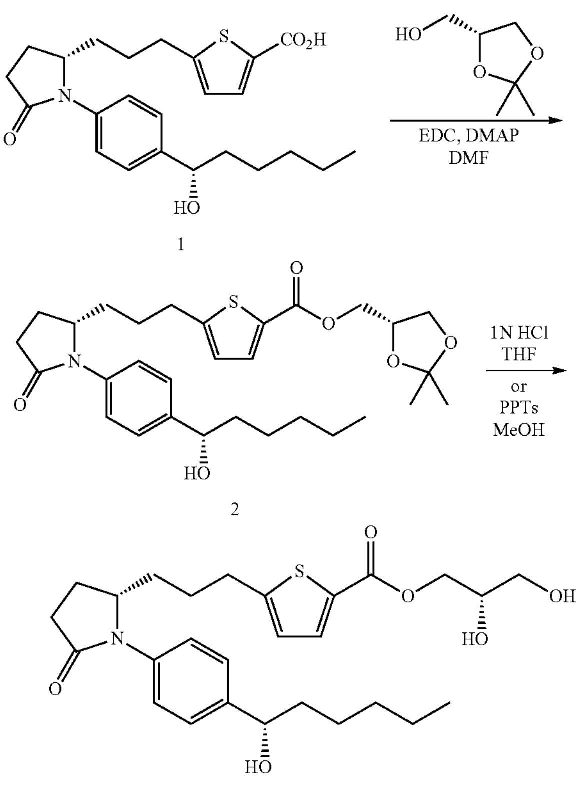

1

2

3

((S)-2,2-dimethyl-1,3-dioxolan-4-yl)methyl 5-(3-((S)-1-(4-((S)-1-hydroxyhexyl)phenyl)-5-oxopyrrolidin-2-yl)propyl)thiophene-2-carboxylate (2). (R)-(−)-2,3-O-Isopropylideneglycerol (307.9 mg, 2.33 mmol) was added to a solution of the carboxylic acid 1 (100 mg, 0.233 mmol), 4-(dimethylamino)pyridine (29.8 mg, 0.243 mmol) and N-(3-dimethylaminopropyl)-N'-ethylcarbodiimide hydrochloride (49.1 mg, 0.256 mmol) in DMF (3.0 mL) at 23° C. After stirring for 16 h the reaction solution was diluted with EtOAc and washed with 1N HCl, saturated aqueous $NaHCO_3$ then brine. The organic portion was dried ($MgSO_4$), filtered and concentrated in vacuo. Purification of the residue by flash column chromatography (silica gel, 1:1 hex/EtOAc followed by 100% EtOAc) afforded 116.8 mg (92%) of acetonide protected ester 2 as a clear, viscous oil.

(S)-2,3-dihydroxypropyl 5-(3-((S)-1-(4-((S)-1-hydroxyhexyl)phenyl)-5-oxopyrrolidin-2-yl)propyl)thiophene-2- carboxylate (3). The ester 2 (116.8 mg, 0.215 mmol) was stirred at 23° C. in a mixture of 1N HCl:THF (1:1, 3.0 mL) for 24 h. The reaction mixture was then diluted with EtOAc and washed with water, saturated aqueous $NaHCO_3$ then brine. The organic portion was dried ($MgSO_4$), filtered and concentrated in vacuo. The residue was purified by flash column chromatography (silica gel, 100% EtOAc followed by 19:1 EtOAc/MeOH) to give 90.7 mg (84%) of the bishydroxy ester 3 as a clear, viscous oil.

Example 2

Synthesis of (R)-2,3-dihydroxypropyl 5-(3-((S)-1-(4-((S)-1-hydroxyhexyl)phenyl)-5-oxopyrrolidin-2-yl)propyl)thiophene-2-carboxylate (5)

((R)-2,2-dimethyl-1,3-dioxolan-4-yl)methyl 5-(3-((S)-1-(4-((S)-1-hydroxyhexyl)phenyl)-5-oxopyrrolidin-2-yl)propyl)thiophene-2-carboxylate (4). In accordance with the procedures described for the preparation of compound 2 above, use of 100 mg (0.233 mmol) of carboxylic acid 1 and 153.9 mg (1.165 mmol) of (S)-(+)-2,3-O-isopropylideneglycerol afforded 118.8 mg (94%) of acetonide protected ester 4, with structure following:

4

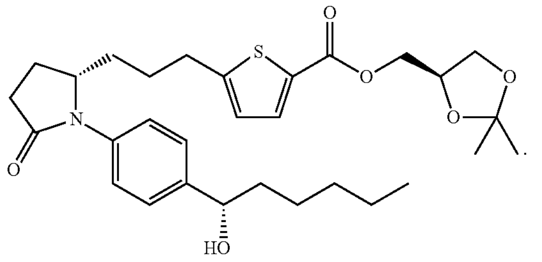

(R)-2,3-dihydroxypropyl 5-(3-((S)-1-(4-((S)-1-hydroxyhexyl)phenyl)-5-oxopyrrolidin-2-yl)propyl)thiophene-2-carboxylate (5). In accordance with the procedures described for the preparation of compound 3 above, use of 50.0 mg (0.0.092 mmol) of ester 4 provided 38.0 mg (82%) of bishydroxy ester 5 as a clear, viscous oil, with structure following:

5

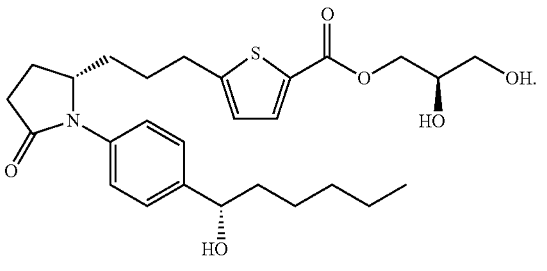

Example 3

Synthesis of 5-(3-((S)-1-(4-((S)-1-((tert-Butyldimethylsilyl)oxy)hexyl) phenyl)-5-oxopyrrolidin-2-yl) propyl)thiophene-2-carboxylic acid (8)

An exemplary synthesis of compound 8 is provided in Scheme 2 following.

Scheme 2

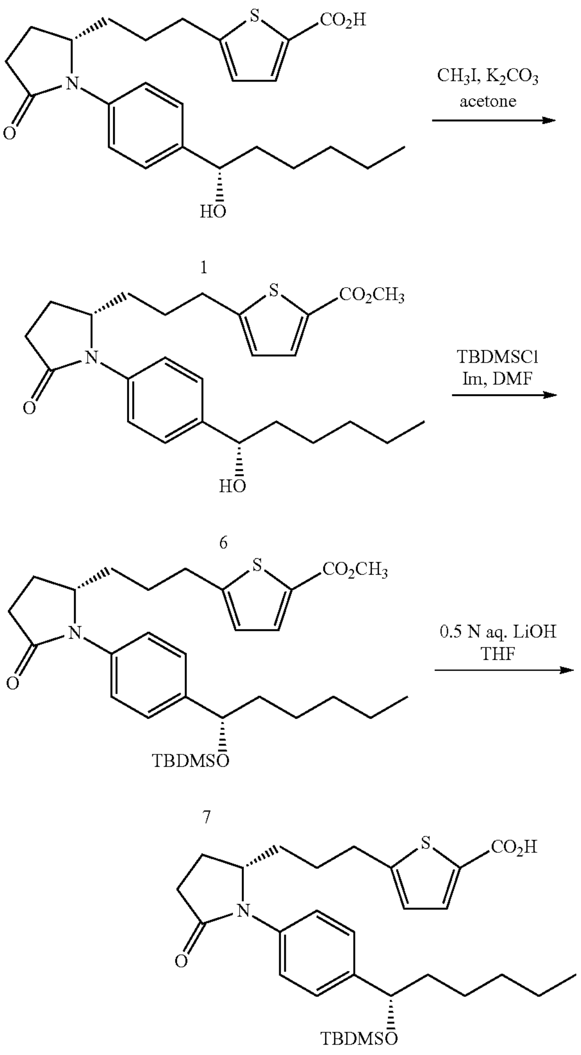

1

6

7

8

Methyl 5-(3-((S)-1-(4-((S)-1-hydroxyhexyl)phenyl)-5-oxopyrrolidin-2-yl)propyl)thiophene-2-carboxylate (6). Iodomethane (0.70 mL, 11.3 mmol) was added to a mixture of the carboxylic acid 1 (485 mg, 1.13 mmol) and potassium carbonate (1.72 g, 12.43 mmol) in DMF (10 mL) at 23° C. The reaction was sealed and stirred for 24 h. The resultant mixture was then diluted with EtOAc and water. The organic portion was separated, washed with brine, dried ($MgSO_4$) filtered and concentrated in vacuo. Flash column chromatography (silica gel, 1:1 hex/EtOAc followed by 100% EtOAc) afforded 496.2 mg (99%) of the methyl ester 6.

Methyl 5-(3-((S)-1-(4-((S)-1-((tert-butyldimethylsilyl)oxy)hexyl)phenyl)-5-oxopyrrolidin-2-yl)propyl)thiophene-2-carboxylate (7). t-Butyldimethylsilylchloride (253.2 mg, 1.68 mmol) was added to a solution of the alcohol 6 (496.2 mg, 1.12 mmol) and imidazole (152.4 mg, 2.24 mmol) in DMF (10 mL) at 23° C. After stirring for 16 h the reaction was diluted with EtOAc and washed with 1N HCl, saturated aqueous $NaHCO_3$ then brine. The organic portion was dried ($MgSO_4$), filtered and concentrated in vacuo. Flash column chromatography (silica gel, 2:1 hex/EtOAc followed by 1:1 hex EtOAc) provided 592 mg (95%) of the silyl ether 7.

5-(3-((S)-1-(4-((S)-1-((tert-Butyldimethylsilyl)oxy)hexyl)phenyl)-5-oxopyrrolidin-2-yl)propyl)thiophene-2-carboxylic acid (8). Lithium hydroxide (4.2 mL of a 0.5 N solution in $H_2O$, 2.12 mmol) was added to a solution of the methyl ester 7 (592 mg, 1.06 mmol) in THF (8.4 mL) at 23° C. The resultant mixture was stirred for 72 h. The reaction was acidified with 1N HCl and then extracted with EtOAc. The organic portion was washed with brine (2×), dried ($Na_2SO_4$), filtered and concentrated in vacuo to give 525.9 mg (91%) of the carboxylic acid 8 as a clear, glue-like substance.

-continued

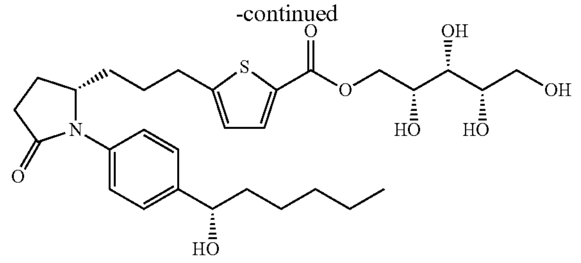

11

Example 4

Synthesis of (2R,3R,4S)-2,3,4,5-Tetrahydroxypentyl 5-(3-((S)-1-(4-((S)-1-hydroxyhexyl)phenyl)-5-oxopyrrolidin-2-yl)propyl)thiophene-2-carboxylate (11)

An exemplary synthesis of compound 11 is provided in Scheme 3 following.

Scheme 3

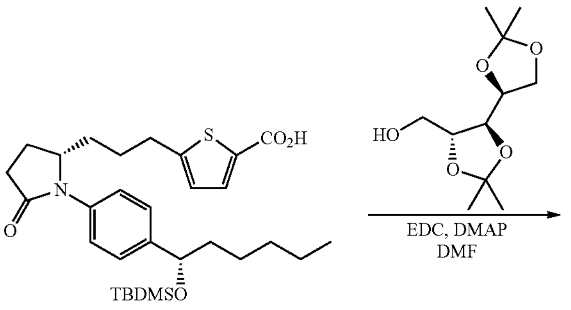

8

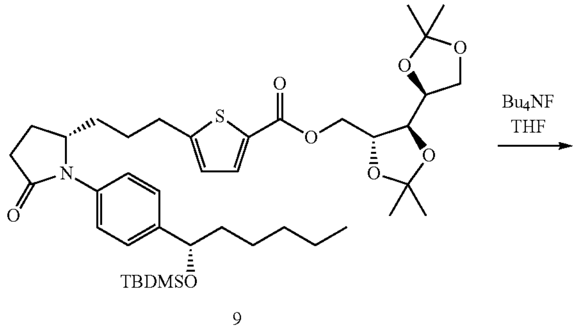

9

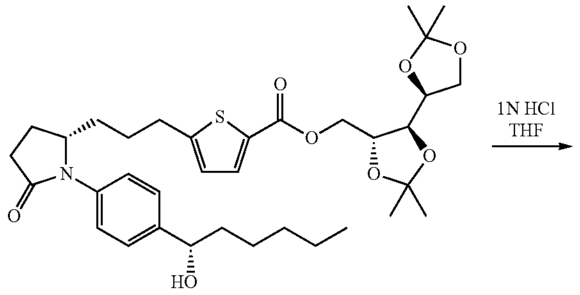

10

((4R,4'S,5R)-2,2,2',2'-Tetramethyl-[4,4'-bi(1,3-dioxolan)]-5-yl)methyl 5-(3-((S)-1-(4-((S)-1-((tert-butyldimethylsilyl)oxy)hexyl)phenyl)-5-oxopyrrolidin-2-yl)propyl) thiophene-2-carboxylate (9). ((4S,4'S,5R)-2,2,2',2'-tetramethyl-[4,4'-bi(1,3-dioxolan)]-5-yl)methanol (76.9 mg, 0.331 mmol) was added to a solution of the carboxylic acid 8 (150 mg, 0.276 mmol), 4-(dimethylamino)pyridine (35.4 mg, 0.289 mmol) and N-(3-dimethylaminopropyl)-N'-ethylcarbodiimide hydrochloride (58.2 mg, 0.303 mmol) in DMF (3.0 mL) at 23° C. After stirring for 72 h the reaction solution was diluted with EtOAc and washed with 1N HCl, saturated aqueous $NaHCO_3$ then brine. The organic portion was dried ($Na_2SO_4$), filtered and concentrated in vacuo. Purification of the residue by flash column chromatorgraphy (silica gel, 1:1 hex/EtOAc) afforded 171.2 mg (82%) of bis-acetonide protected ester 9 as a clear, viscous oil.

((4R,4'S,5R)-2,2,2',2'-Tetramethyl-[4,4'-bi(1,3-dioxolan)]-5-yl)methyl 5-(3-((S)-1-(4-((S)-1-hydroxyhexyl)phenyl)-5-oxopyrrolidin-2-yl)propyl)thiophene-2-carboxylate (10). Tetrabutylammonium fluoride (0.34 mL of a 1.0 M solution in THF, 0.339 mmol) was added to a solution of the silyl ether 9 (171.2 mg, 0.226 mmol) in THF (3.0 mL) at 23° C. After 48 h the reaction was diluted with EtOAc and washed with $H_2O$ followed by brine. The organic portion was dried ($MgSO_4$), filtered and concentrated in vacuo. Flash column chromatography (silica gel, 1:1 hex/EtOAc followed by 100% EtOAc) afforded 137.0 mg (94%) of the hydroxy ester 10.

(2R,3R,4S)-2,3,4,5-Tetrahydroxypentyl 5-(3-((S)-1-(4-((S)-1-hydroxyhexyl)phenyl)-5-oxopyrrolidin-2-yl)propyl) thiophene-2-carboxylate (11). The bis-acetonide 10 (45.0 mg, 0.070 mmol) was stirred at 23° C. in a mixture of 1N HCl:THF (1:1, 3.0 mL) for 48 h. The reaction mixture was then diluted with EtOAc and washed with water, saturated aqueous $NaHCO_3$ then brine. The organic portion was dried ($Na_2SO_4$), filtered and concentrated in vacuo to give 32.9 mg (83%) of the ester 11 as a clear, viscous oil.

Example 5

Synthesis of (2R,3R,4S,5R)-2,3,4,5,6-Pentahydroxyhexyl 5-(3-((S)-1-(4-((S)-1-hydroxyhexyl)phenyl)-5-oxopyrrolidin-2-yl)propyl)thiophene-2-carboxylate (14)

(S)-2-Hydroxy-2-((4R,4'R,5R)-2,2,2',2'-tetramethyl-[4,4'-bi(1,3-dioxolan)]-5-yl)ethyl 5-(3-((S)-1-(4-((S)-1-((tert-butyldimethylsilyl)oxy)hexyl)phenyl)-5-oxopyrrolidin-2-yl)propyl)thiophene-2-carboxylate (12). In accordance with the procedures described for the preparation of compound 9 above, use of 100 mg (0.184 mmol) of carboxylic acid 8 and 57.8 mg (0.221 mmol) of (S)-1-((4R,4'R,5R)-2,2,2',2'-tetramethyl-[4,4'-bi(1,3-dioxolan)]-5-yl)ethane-1,2-diol afforded 92.0 mg (64%) of bisacetonide protected ester 12, with structure following:

12

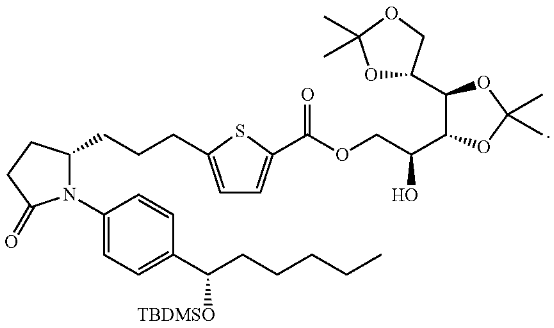

(S)-2-hydroxy-2-((4R,4'R,5R)-2,2,2',2'-tetramethyl-[4,4'-bi(1,3-dioxolan)]-5-yl)ethyl 5-(3-((S)-1-(4-((S)-1-hydroxyhexyl)phenyl)-5-oxopyrrolidin-2-yl)propyl)thiophene-2-carboxylate (13). In accordance with the procedures described for the preparation of compound 10 above, use of 92.0 mg (0.117 mmol) of silyl ether 12 provided 70.8 mg (90%) of hydroxy-ester 13, with structure following:

13

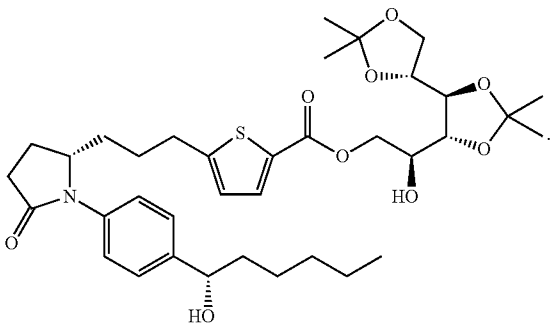

(2R,3R,4S,5R)-2,3,4,5,6-Pentahydroxyhexyl 5-(3-((S)-1-(4-((S)-1-hydroxyhexyl)phenyl)-5-oxopyrrolidin-2-yl)propyl)thiophene-2-carboxylate (14). In accordance with the procedures described for the preparation of compound 11 above, use of 45.0 mg (0.067 mmol) of bis-acetonide 13 provided 33.3 mg (84%) of ester 14 as a clear, viscous oil, with structure following:

14

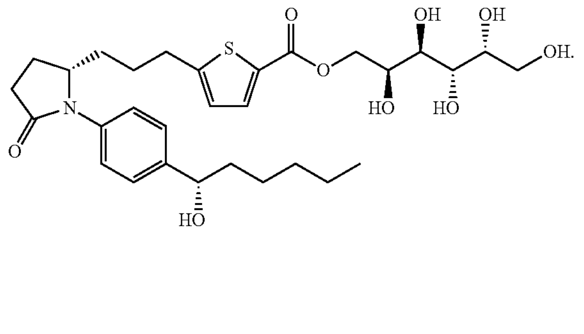

Example 6

Synthesis of (2S,3 S)-2,3,4-Trihydroxybutyl 5-(3-((S)-1-(4-((S)-1-hydroxyhexyl)phenyl)-5-oxopyrrolidin-2-yl)propyl)thiophene-2-carboxylate (17)

((4S,5S)-5-(Hydroxymethyl)-2,2-dimethyl-1,3-dioxolan-4-yl)methyl 5-(3-((S)-1-(4-((S)-1-((tert-butyldimethylsilyl)oxy)hexyl)phenyl)-5-oxopyrrolidin-2-yl)propyl)thiophene-2-carboxylate (15). In accordance with the procedures described for the preparation of compound 9 above, use of 128 mg (0.235 mmol) of carboxylic acid 8 and 57.3 mg (0.353 mmol) of (+)-2,3-O-isopropylidene-L-threitol afforded 116.7 mg (72%) of acetonide 15, with structure following:

15

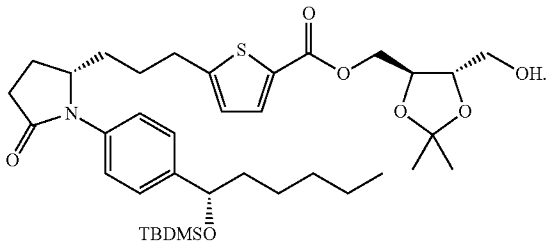

((4S,5S)-5-(hydroxymethyl)-2,2-dimethyl-1,3-dioxolan-4-yl)methyl 5-(3-((S)-1-(4-((S)-1-hydroxyhexyl)phenyl)-5-oxopyrrolidin-2-yl)propyl)thiophene-2-carboxylate (16). In accordance with the procedures described for the preparation of compound 10 above, use of 116.7 mg (0.170 mmol) of silyl ether 15 provided 55.0 mg (56%) of hydroxy-ester 16, with structure following:

16

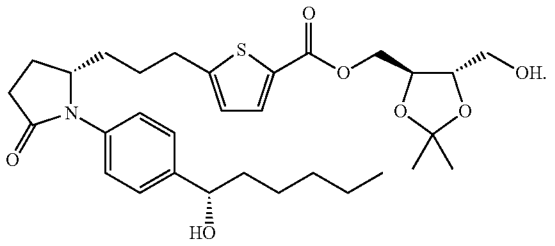

(2S,3S)-2,3,4-Trihydroxybutyl 5-(3-((S)-1-(4-((S)-1-hydroxyhexyl)phenyl)-5-oxopyrrolidin-2-yl)propyl)thiophene-2-carboxylate (17). In accordance with the procedures described for the preparation of compound 11 above, use of 55.0 mg (0.096 mmol) of acetonide 16 provided 28.0 mg (55%) of ester 17 as a clear, viscous oil, with structure following:

17

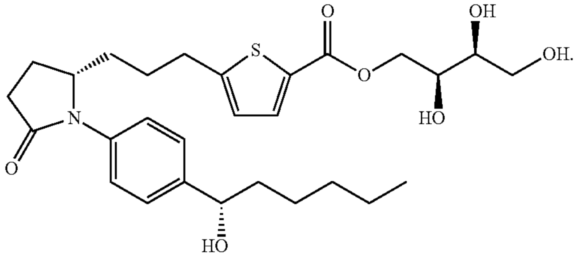

Example 7

Synthesis of (2R,3R)-2,3,4-Trihydroxybutyl 5-(3-((S)-1-(4-((S)-1-hydroxyhexyl)phenyl)-5-oxopyrrolidin-2-yl)propyl)thiophene-2-carboxylate (20)

((4R,5R)-5-(Hydroxymethyl)-2,2-dimethyl-1,3-dioxolan-4-yl)methyl 5-(3-((S)-1-(4-((S)-1-((tert-butyldimethylsilyl)oxy)hexyl)phenyl)-5-oxopyrrolidin-2-yl)propyl)thiophene-2-carboxylate (18). In accordance with the procedures described for the preparation of compound 9 above, use of 166 mg (0.305 mmol) of carboxylic acid 8 and 74.4 mg (0.456 mmol) of (−)-2,3-O-isopropylidene-D-threitol afforded 116.1 mg (55%) of acetonide 18, with structure following:

18

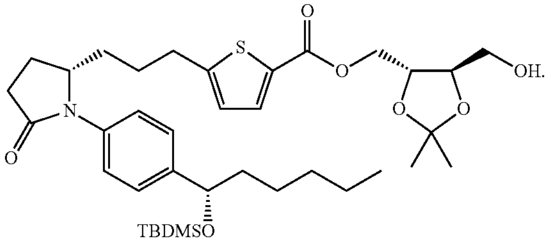

((4R,5R)-5-(Hydroxymethyl)-2,2-dimethyl-1,3-dioxolan-4-yl)methyl 5-(3-((S)-1-(4-((S)-1-hydroxyhexyl)phenyl)-5-oxopyrrolidin-2-yl)propyl)thiophene-2-carboxylate (19). In accordance with the procedures described for the preparation of compound 10 above, use of 116.1 mg (0.169 mmol) of silyl ether 18 provided 50.0 mg (52%) of hydroxy-ester 19, with structure following:

19

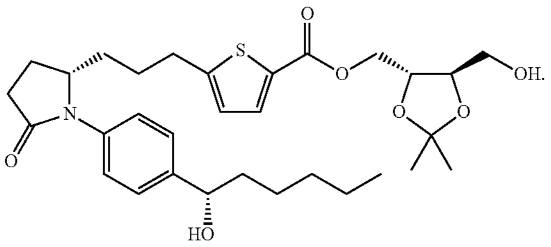

(2R,3R)-2,3,4-Trihydroxybutyl 5-(3-((S)-1-(4-((S)-1-hydroxyhexyl)phenyl)-5-oxopyrrolidin-2-yl)propyl)thiophene-2-carboxylate (20). In accordance with the procedures described for the preparation of compound 11 above, use of 50.0 mg (0.087 mmol) of acetonide 19 provided 45.6 mg (98%) of ester 20 as a clear, viscous oil, with structure following:

20

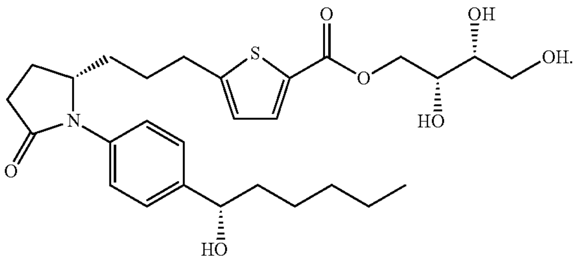

Example 8

Exemplary Aqueous Stability

The compound of Formula (IIIa):

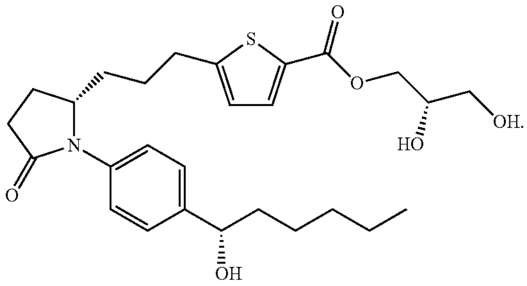

was selected as an exemplary compound for evaluation of aqueous stability. In particular, the aqueous stability of the compound of Formula (Ma) upon storage in aqueous solution at several temperatures for several weeks was evaluated by HPLC using the following conditions:

Column: BioWidePore C18 (SUPELCO), 4.6 mm×25 cm, 5 μm

Mobile Phase A: 0.1% (V/V) trifluoroacetic acid (TFA) in di-water, 0.8 micron filtered Mobile Phase B: 100% acetonitrile, 0.8 micron filtered Column temp: Ambient Injection volume: 30 μL UV Detection: 214 nm Flow: 1.0 mL/min Run time: 25 minutes Sample diluent: 50% acetonitrile in di-water Gradient condition: See Table 1

TABLE 1

| Time (min) | % of B |
|---|---|
| 0.0 | 20.0 |
| 1.0 | 20.0 |
| 16.0 | 90.0 |
| 18.0 | 90.0 |
| 19.0 | 20.0 |
| 25.0 | 20.0 |

and compared to a standard shown below:

(standard)

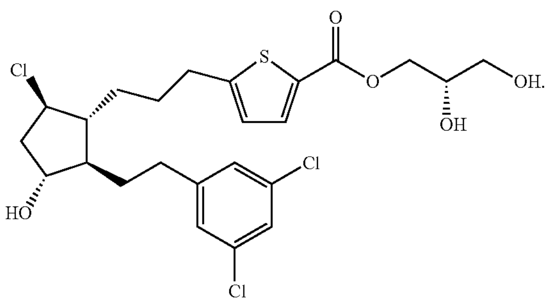

The results of the stability study are shown in Table 2 below.

TABLE 2

| | % Recovery vs. $T_0$ | | | | |
|---|---|---|---|---|---|
| Compound | Storage Condition | $T_0$ | Week-1 | Week-2 | Week-4 |
| Standard | 25° C. | 100.0 | 100.1 | 101.0 | 101.6 |
| | 40° C. | 100.0 | 100.1 | 100.1 | 98.6 |
| | 60° C. | 100.0 | 99.3 | 97.5 | 95.6 |
| Formula (IIIa) | 25° C. | 100.0 | 100.8 | 100.4 | 102.6 |
| | 40° C. | 100.0 | 100.6 | 99.8 | 101.8 |
| | 60° C. | 100.0 | 99.0 | 97.4 | 96.3 |

The above results are exemplary, and based on them, the compounds described herein are expected to have similar characteristics to those of the compound of Formula (IIIa).

V. Exemplary Embodiments

Embodiment 1

A compound having the structure of Formula (I):

(I)

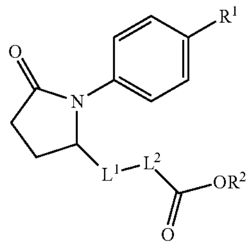

or pharmaceutically acceptable salt thereof, wherein, $R^1$ is unsubstituted $C_1$-$C_{10}$ alkyl, $C_1$-$C_{10}$ alkyl substituted by $R^{1A}$, unsubstituted 2 to 10 membered heteroalkyl, or 2 to 10 membered heteroalkyl substituted by $R^{1A}$;

$R^{1A}$ is hydroxyl or halogen;

$L^1$ is a bond, $C_1$-$C_{10}$ alkylene, 2 to 10 membered heteroalkylene;

$L^2$ is a bond, $C_1$-$C_{10}$ alkylene, arylene, or heteroarylene;

$R^2$ is substituted or unsubstituted alkyl, substituted or unsubstituted heteroalkyl, substituted or unsubstituted cycloalkyl, substituted or unsubstituted hetercycloalkyl, substituted or unsubstituted aryl, or substituted or unsubstituted heteroaryl.

Embodiment 2

The compound of Embodiment 1, wherein $R^1$ is $C_1$-$C_{10}$ alkyl substituted by $R^{1A}$ or 2 to 10 membered heteroalkyl substituted by R.

Embodiment 3

The compound of Embodiment 2, wherein $R^{1A}$ is hydroxyl or fluoro.

Embodiment 4

The compound of Embodiment 3, wherein $R^{1A}$ is hydroxyl.

Embodiment 5

The compound of any one of Embodiments 1 to 4, wherein $R^1$ is $C_1$-$C_{10}$ alkyl substituted by $R^{1A}$ and wherein $R^{1A}$ is hydroxyl.

Embodiment 6

The compound of any one of Embodiments 1 to 5, wherein $L^1$ is substituted or unsubstituted $C_1$-$C_6$ alkylene.

Embodiment 7

The compound of any one of Embodiments 1 to 6, wherein $L^1$ is unsubstituted $C_1$-$C_6$ alkylene.

Embodiment 8

The compound of any one of Embodiments 1 to 6, wherein $L^1$ is substituted or unsubstituted propylene.

Embodiment 9

The compound of any one of Embodiments 1 to 5, wherein $L^1$ is $C_1$-$C_{10}$ alkylene substituted by $L^{1A}$, or 2 to 10 membered heteroalkylene substituted by $L^{1A}$, wherein $L^{1A}$ at each occurrence is independently halogen or hydroxyl.

Embodiment 10

The compound of Embodiment 9, wherein $L^{1A}$ is hydroxyl.

Embodiment 11

The compound of Embodiment 9, wherein $L^{1A}$ is fluoro.

Embodiment 12

The compound of Embodiment 9, wherein $L^1$ is $C_1$-$C_{10}$ alkylene substituted by $L^{1A}$.

Embodiment 13

The compound of Embodiment 12, wherein $L^{1A}$ is hydroxyl.

Embodiment 14

The compound of Embodiment 12, wherein $L^{1A}$ is fluoro.

Embodiment 15

The compound of Embodiment 9, wherein $L^1$ is $C_2$-$C_6$ alkylene substituted by $L^{1A}$.

Embodiment 16

The compound of Embodiment 15, wherein $L^{1A}$ is hydroxy.

Embodiment 17

The compound of Embodiment 15, wherein $L^{1A}$ is fluoro.

Embodiment 18

The compound of Embodiment 9, wherein $L^1$ is unsubstituted $C_2$-$C_6$ alkylene.

Embodiment 19

The compound of Embodiment 9, wherein $L^1$ is unsubstituted propylene.

Embodiment 20

The compound of any one of Embodiments 1 to 19, wherein $L^2$ is substituted or unsubstituted $C_1$-$C_{10}$ alkylene, substituted or unsubstituted arylene or substituted or unsubstituted heteroarylene.

Embodiment 21

The compound of any one of Embodiments 1 to 20, wherein $L^2$ is $C_1$-$C_{10}$ alkylene substituted by $L^{2A}$, arylene substituted by $L^{2A}$, or heteroarylene substituted by $L^{2A}$, wherein $L^{2A}$ is hydroxyl or halogen.

Embodiment 22

The compound of Embodiment 21, wherein $L^2$ is heteroarylene substituted by $L^{2A}$.

Embodiment 23

The compound of any one of Embodiments 1 to 20, wherein $L^2$ is unsubstituted $C_1$-$C_{10}$ alkylene, unsubstituted arylene, or unsubstituted heteroarylene.

Embodiment 24

The compound of any one of Embodiments 1 to 20, wherein $L^2$ is unsubstituted heteroarylene.

Embodiment 25

The compound of Embodiment 24, wherein $L^2$ is unsubstituted pyridinylene, unsubstituted thiophenylene, unsubstituted pyrrolylene, or unsubstituted furanylene.

Embodiment 26

The compound of any one of Embodiments 1 to 25, wherein $R^2$ is unsubstituted $C_1$-$C_{10}$ alkyl, $C_1$-$C_{10}$ alkyl substituted by $R^{2A}$, unsubstituted 2 to 10 membered heteroalkyl, or 2 to 10 membered heteroalkyl substituted by $R^{2A}$;

wherein:

$R^{2A}$ at each occurrence is independently halogen, hydroxyl, unsubstituted alkyl, alkyl substituted by $R^{2B}$, unsubstituted heteroalkyl, heteroalky substituted by $R^{2B}$, unsubstituted cycloalkyl, cycloalkyl substituted by $R^{2B}$, unsubstituted heterocycloalkyl, heterocycloalkyl substituted by $R^{2B}$, unsubstituted aryl, aryl substituted by $R^{2B}$, unsubstituted heteroaryl, or heteroaryl substituted by $R^{2B}$;

$R^{2B}$ at each occurrence is independently halogen, hydroxyl, unsubstituted alkyl, alkyl substituted by $R^{2C}$, unsubstituted heteroalkyl, heteroalky substituted by $R^{2C}$, unsubstituted cycloalkyl, cycloalkyl substituted by $R^{2C}$, unsubstituted heterocycloalkyl, heterocycloalkyl substituted by $R^{2C}$, unsubstituted aryl, aryl substituted by $R^{2C}$, unsubstituted heteroaryl, or heteroaryl substituted by $R^{2C}$;

$R^{2C}$ at each occurrence is independently halogen, hydroxyl, unsubstituted alkyl, unsubstituted heteroalkyl, unsubstituted cycloalkyl, unsubstituted heterocycloalkyl, unsubstituted aryl or unsubstituted heteroaryl.

Embodiment 27

The compound Embodiment 26, wherein $R^2$ is unsubstituted $C_1$-$C_{10}$ alkyl or $C_1$-$C_{10}$ alkyl substituted by $R^{2A}$.

Embodiment 28

The compound of any one of Embodiments 26 to 27, wherein $R^{2A}$ is unsubstituted alkyl, alkyl substituted by $R^{2B}$, unsubstituted heteroalkyl, or heteroalkyl substituted by $R^{2B}$.

Embodiment 29

The compound of any one of Embodiments 26 to 28, wherein $R^{2A}$ is unsubstituted alkyl or alkyl substituted by $R^{2B}$.

Embodiment 30

The compound of any one of Embodiments 26 to 29, wherein $R^{2A}$ is halogen or hydroxyl.

Embodiment 31

The compound of Embodiment 30, wherein $R^{2A}$ is hydroxyl.

Embodiment 32

The compound of any one of Embodiments 1 to 31, wherein $L^2$ is thiophene-2,5-diyl.

Embodiment 33

The compound of any one of Embodiments 1 to 32, wherein $L^1$ is propylene-1,3-diyl.

Embodiment 34

The compound of Embodiment 33, having the structure of Formula (II):

(II)

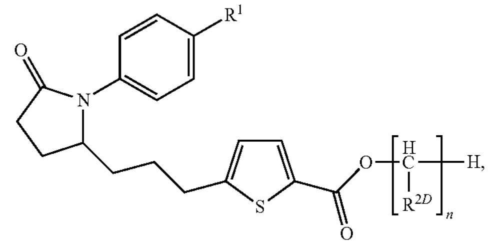

wherein:

n is 1 to 10; and $R^{2D}$ at each occurrence is independently hydrogen or hydroxyl.

Embodiment 35

The compound of Embodiment 34, wherein $R^1$ is $—CHOH(CH_2)_4CH_3$.

Embodiment 36

The compound of Embodiment 34 or 35 having the structure of Formula (III):

(III)

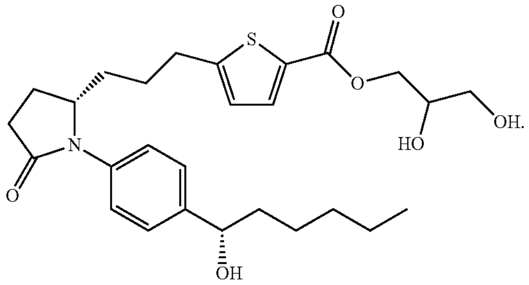

Embodiment 37

The compound of Embodiment 36 having the structure of Formula (IIIa) or (IIIb):

(IIIa)

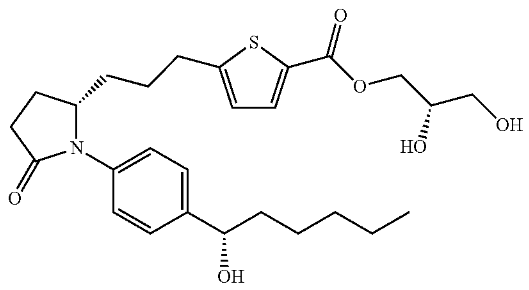

-continued (IIIb)

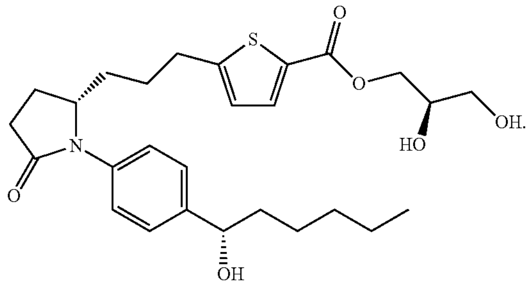

Embodiment 38

The compound of Embodiment 34 or 35 having the structure of Formula (IV):

(IV)

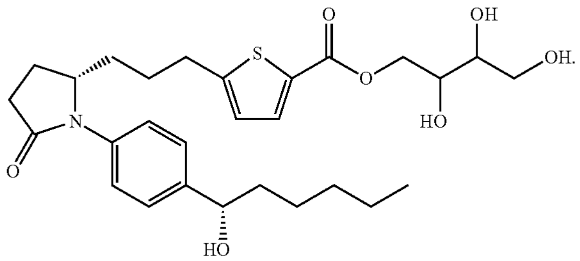

Embodiment 39

The compound of Embodiment 38 having the structure of Formula (Iva), (IVb), (IVc), or (IVd):

(IVa)

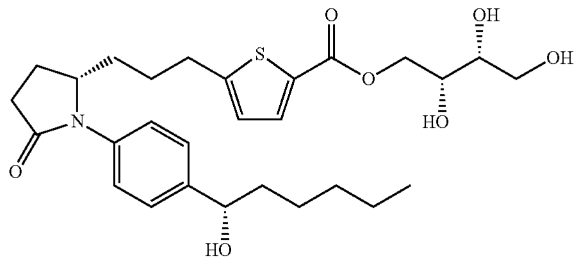

(IVb)

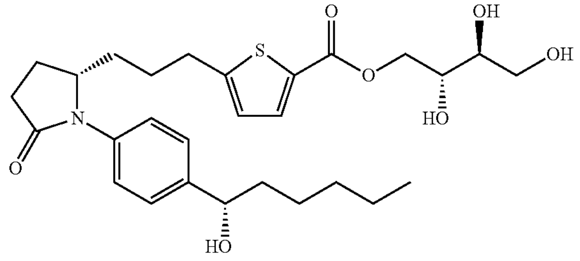

-continued
(IVc)
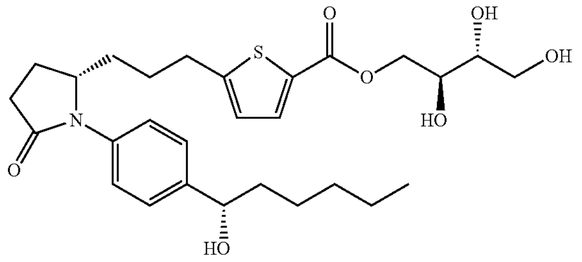
(IVd)
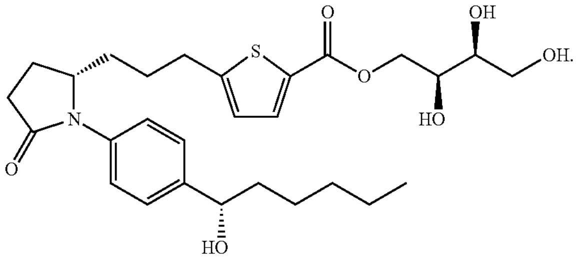
Embodiment 40
The compound of Embodiment 34 or 35 having the structure of Formula (V):
(V)
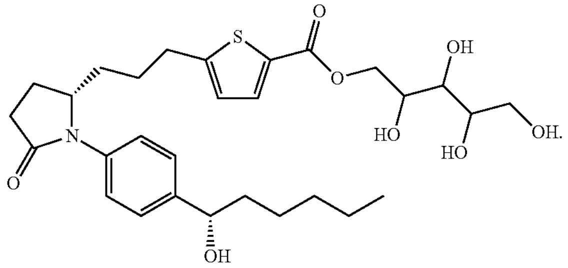
Embodiment 41
The compound of Embodiment 40 having the structure of Formula (Va), (Vb), (Vc), (Vd), (Ve), (Vf), (Vg), or (Vh):
(Va)
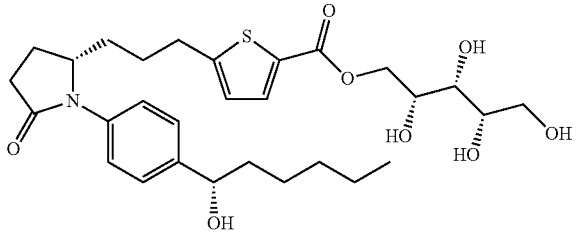
-continued
(Vb)
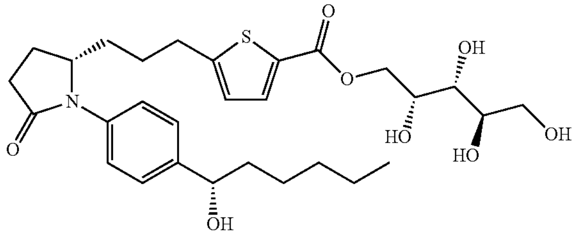
(Vc)
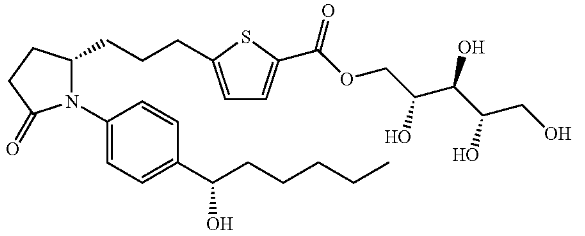
(Vd)
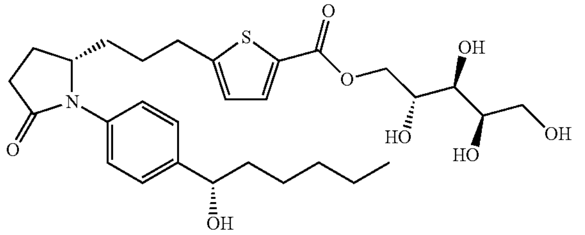
(Ve)
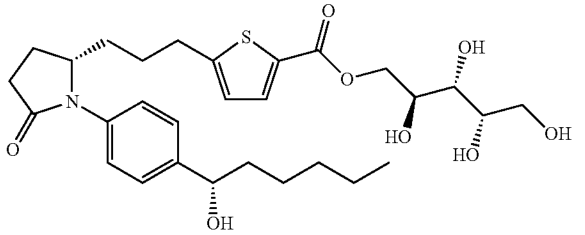
(Vf)
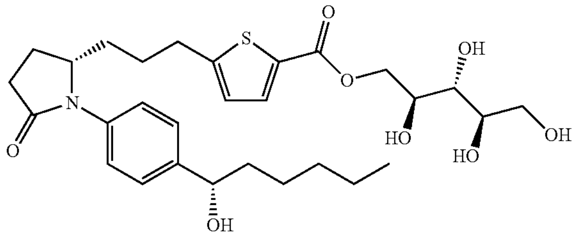
(Vg)
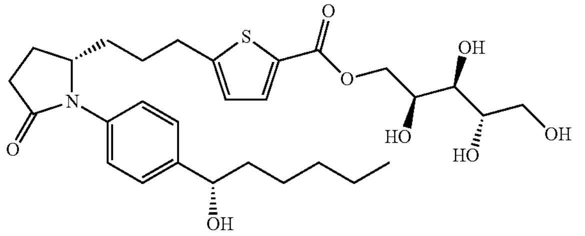
or -continued
(Vh)
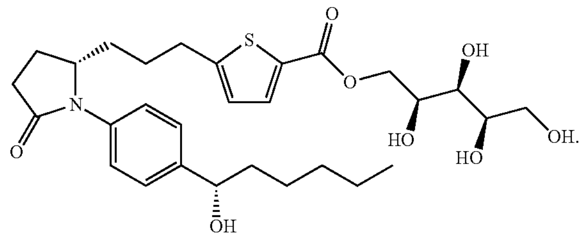
Embodiment 42
The compound of Embodiment 34 or 35 having the structure of Formula (VI):
(VI)
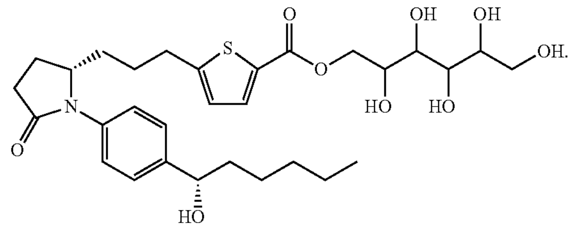
Embodiment 43
The compound of Embodiment 42 having the structure of Formula (VIa), (VIb), (VIc), (VId), (VIe), (VIf), (VIg), (VIh), (VIi), (VIj), (VIk), (VIl), (VIm), (VIn), (VIo), or (VIp):
(VIa)
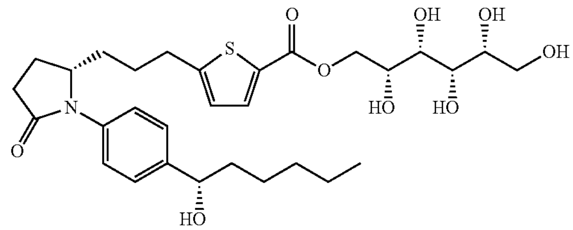
(VIb)
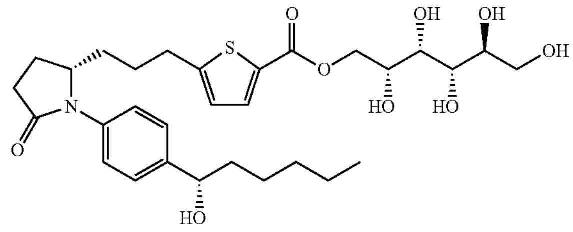
-continued
(VIc)
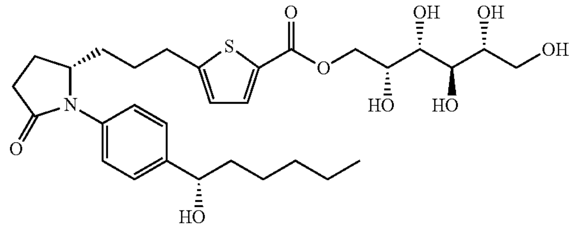
(VId)
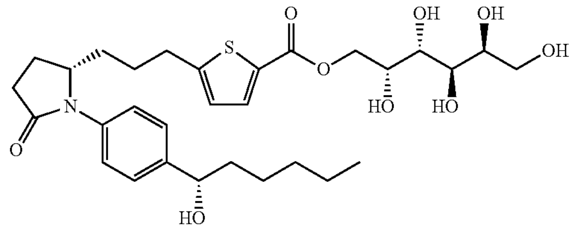
(VIe)
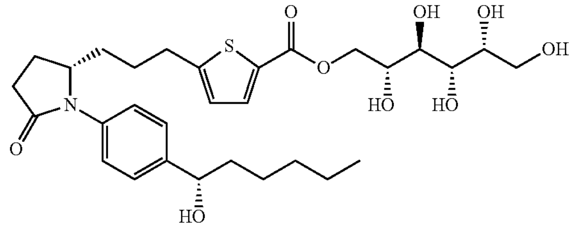
(VIf)
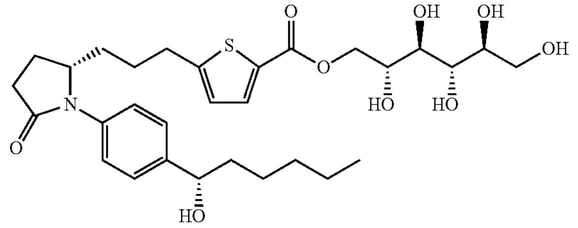
(VIg)
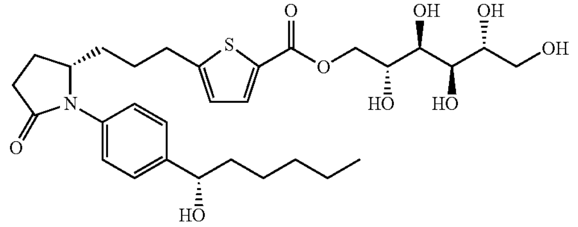
(VIh)
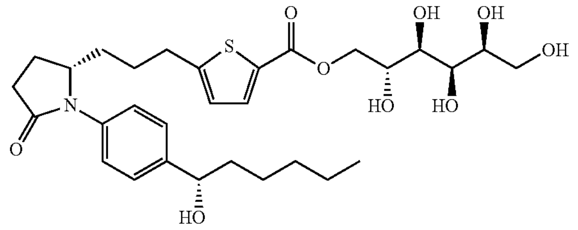

-continued (VIi)

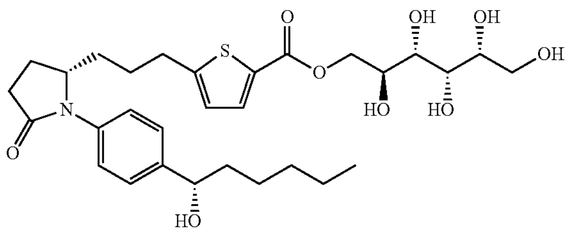

(VIj)

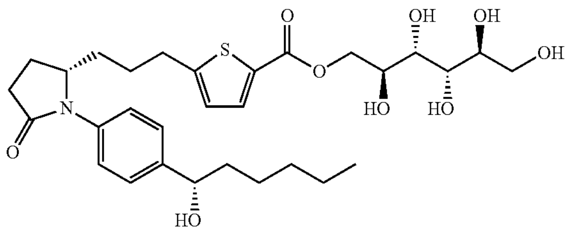

(VIk)

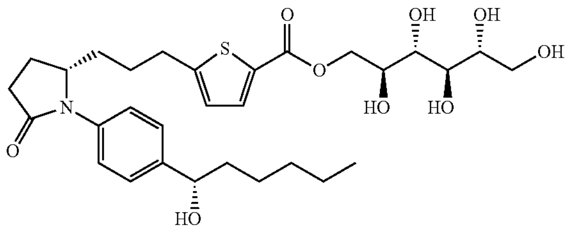

(VIl)

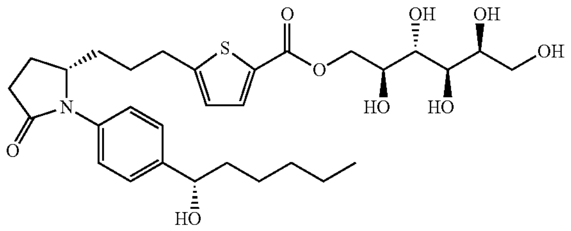

(VIm)

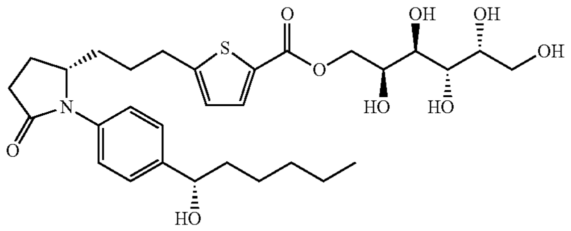

(VIn)

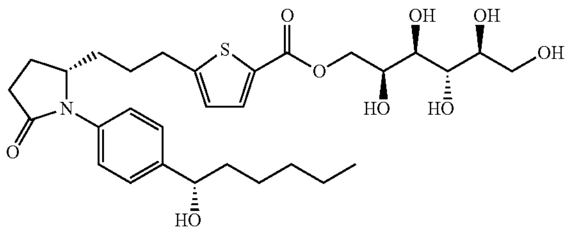

-continued (VIo)

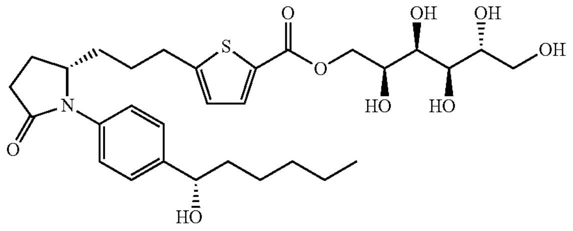

(VIp)

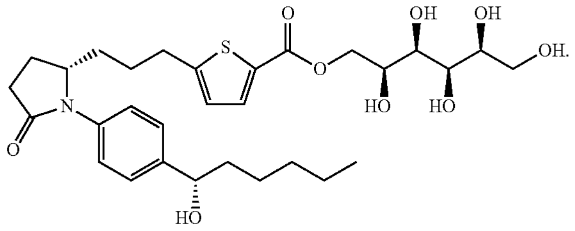

Embodiment 44

An ophthalmic pharmaceutical composition comprising the compound of any one of Embodiments 1 to 43 and an ophthalmically acceptable excipient.

Embodiment 45

A method of treating an ophthalmic disease in a subject, said method comprising administering a therapeutically effective amount of a compound of any one of Embodiments 1 to 43 to a subject in need thereof.

Embodiment 46

The method of Embodiment 45, wherein said administering is topical ocular administering.

Embodiment 47

The method of Embodiment 45, wherein said disease is glaucoma.

Embodiment 48

The method of Embodiment 45, wherein said disease is macular degeneration.

Embodiment 49

The method of Embodiment 45, wherein said disease results from increased intraocular pressure.

Embodiment 50

A method of reducing corneal thickening, said method comprising administering a therapeutically effective amount of a compound of any one of Embodiments 1 to 43 to a subject in need thereof.

Embodiment 51

The method of Embodiment 50, wherein said subject suffers from glaucoma.

Embodiment 52

The method of Embodiment 50, wherein said subject suffers from ocular hypertension.

Embodiment 54

Use of a compound of any one of Embodiments 1 to 43 in the manufacture of a medicament for the treatment an ophthalmic disease.

Embodiment 55

The use of Embodiment 54 wherein said ophthalmic disease is selected from the group consisting of glaucoma, macular degeneration, and increased intraocular pressure.

Embodiment 56

Use of a compound of any one of Embodiments 1 to 43 in the manufacture of a medicament for reducing corneal thickening.

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated. To the extent that any recitations in the incorporated references conflict with any recitations herein, the recitations herein will control.

The foregoing descriptions details ester prodrugs of gamma-lactam compounds and methods of use of such compounds for the treatment of ocular diseases including, among other things, glaucoma and macular degeneration, and represents the best mode contemplated. It should not be construed as limiting the overall scope hereof; rather, the ambit of the present disclosure is to be governed only by the lawful construction of the appended claims.

What is claimed is:

1. A compound of Formula (II):

(II)

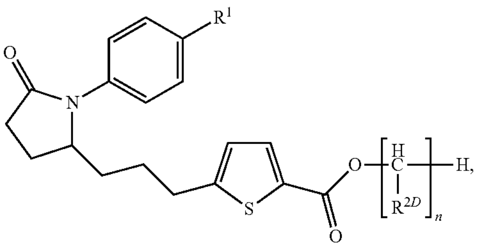

wherein:

$R^1$ is unsubstituted $C_1$-$C_{10}$ alkyl, $C_1$-$C_{10}$ alkyl substituted by $R^{1A}$, unsubstituted 2 to 10 membered heteroalkyl, or 2 to 10 membered heteroalkyl substituted by $R^{1A}$;

$R^{1A}$ is hydroxyl or halogen; and n is 3, 4, 5, or 6;

$R^{2D}$ at each occurrence is independently hydrogen or hydroxyl, and wherein 2, 3, 4, or 5 substituents $R^{2D}$ are not hydrogen.

2. The compound of claim 1, wherein $R^1$ is $CHOH(CH_2)_4CH_3$.

3. The compound of claim 1 of Formula (III):

(III)

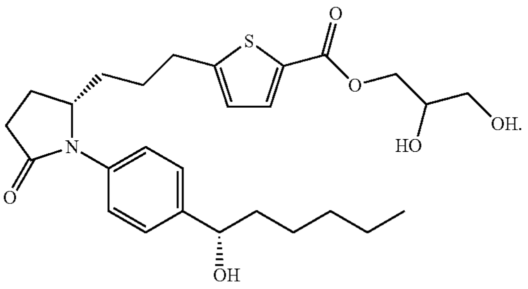

4. The compound of claim 3 of Formula (IIIa) or (IIIb):

(IIIa)

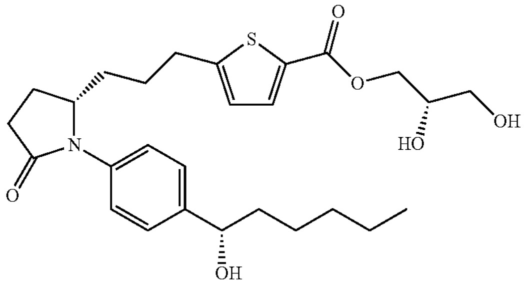

(IIIb)

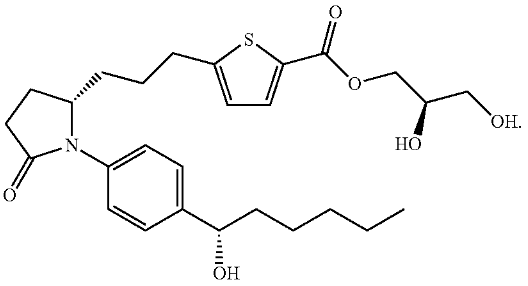

5. The compound of claim 1 of Formula (IV):

(IV)

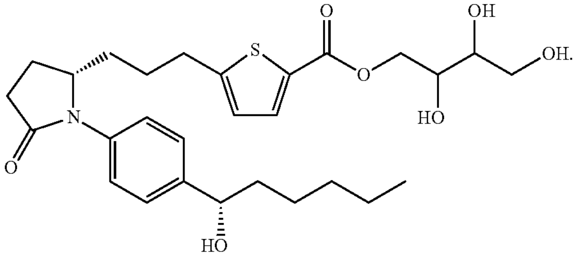

6. The compound of claim 5 of Formula (Iva), (IVb), (IVc), or (IVd):
(IVa)
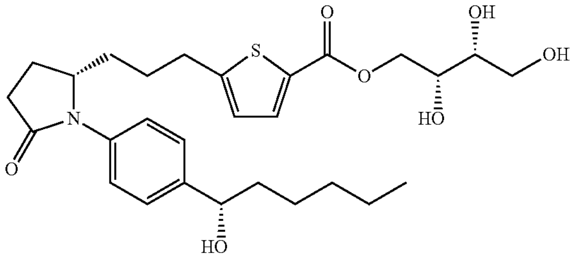
(IVb)
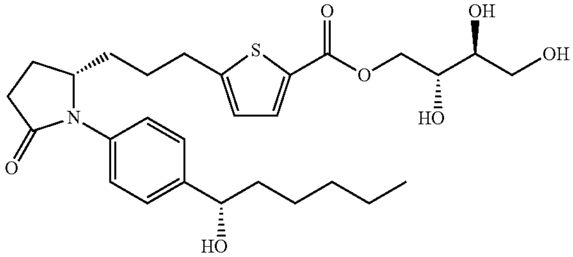
(IVc)
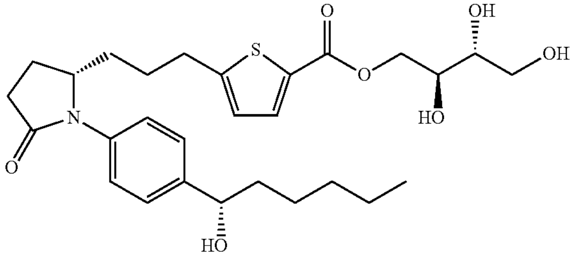
(IVd)
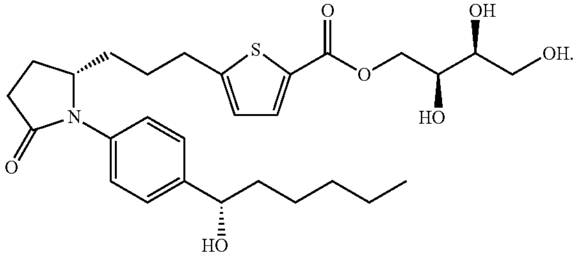
7. The compound of claim 1 of Formula (V):
(V)
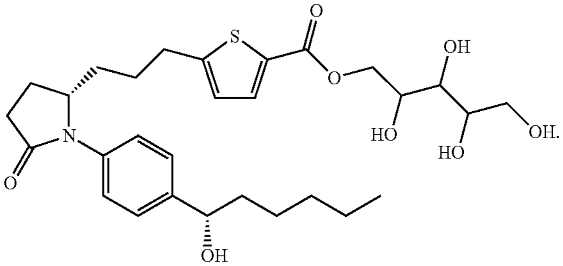
8. The compound of claim 7 of Formula (Va), (Vb), (Vc), (Vd), (Ve), (Vf), (Vg), or (Vh):
(Va)
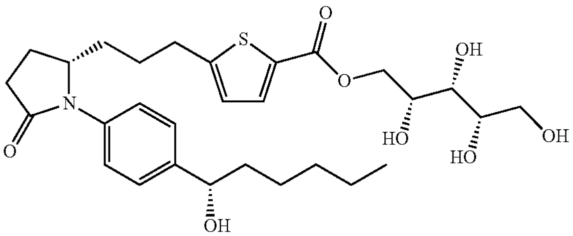
(Vb)
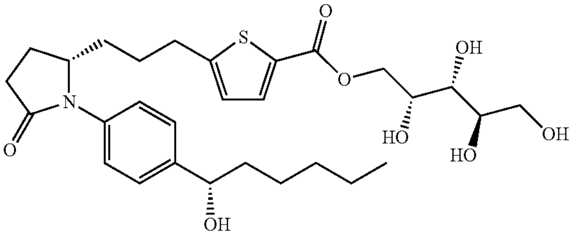
(Vc)
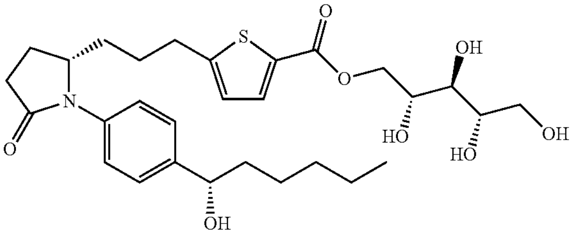
(Vd)
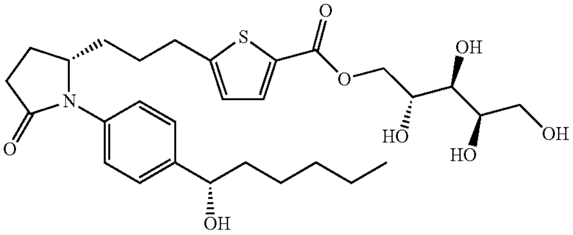
(Ve)
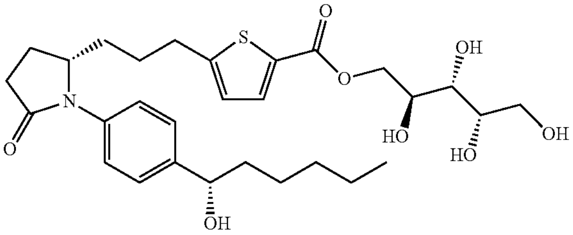
(Vf)
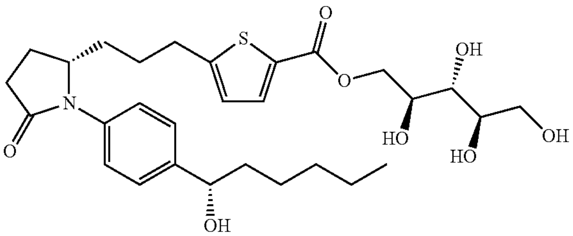

-continued
(Vg)
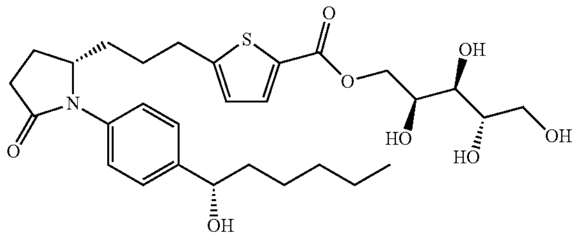
(Vh)
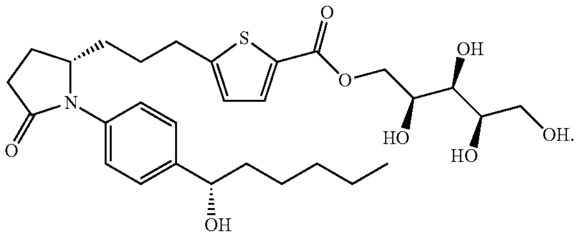
9. The compound of claim 1 of Formula (VI):
(VI)
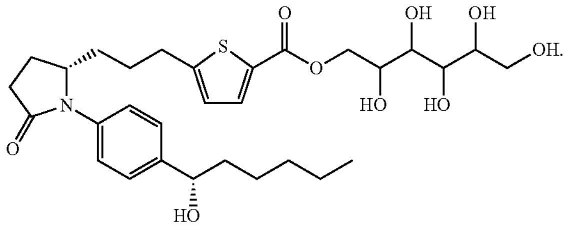
10. The compound of claim 9 of Formula (VIa), (VIb), (VIc), (VId), (VIe), (VIf), (VIg), (VIh), (Vii), (VIj), (VIk), (VIl), (VIm), (VIn), (VIo), or (VIp):
(VIa)
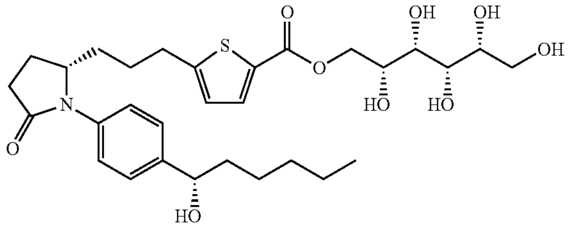
(VIb)
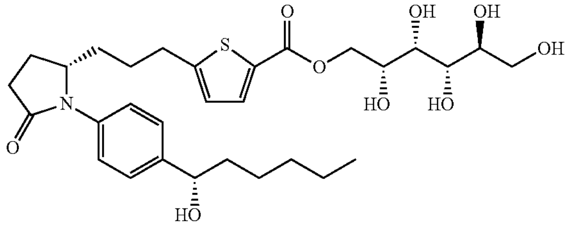
-continued
(VIc)
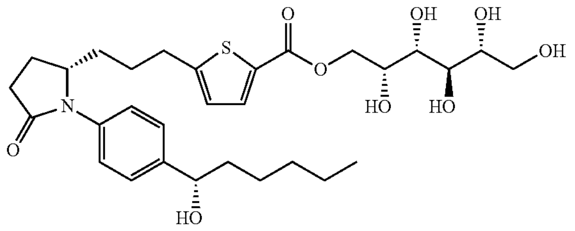
(VId)
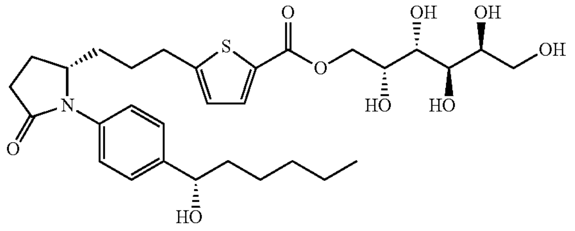
(VIe)
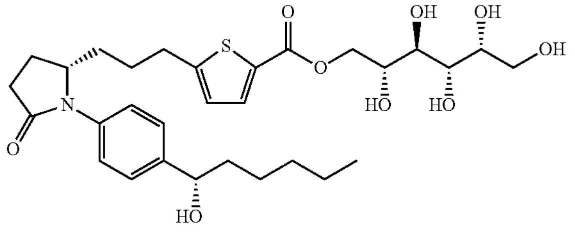
(VIf)
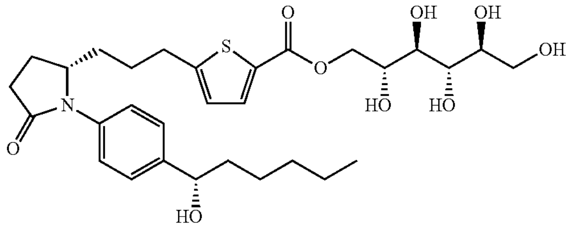
(VIg)
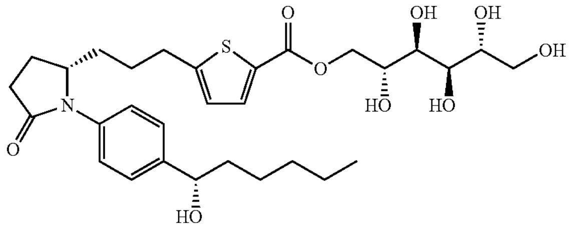
(VIh)
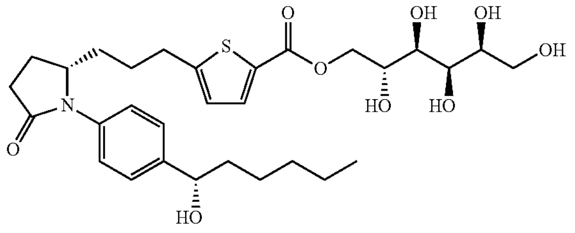

-continued (VIi)

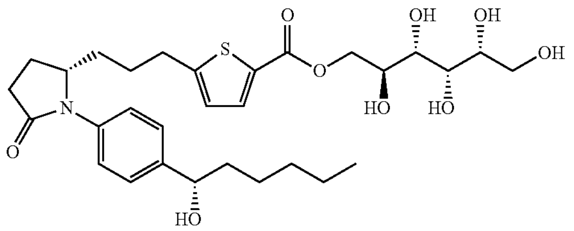

(VIj)

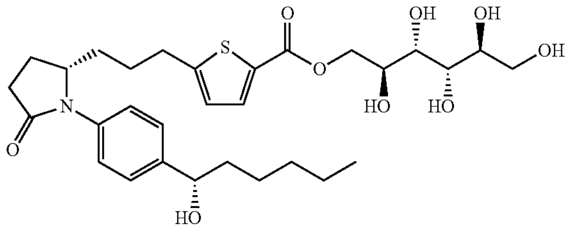

(VIk)

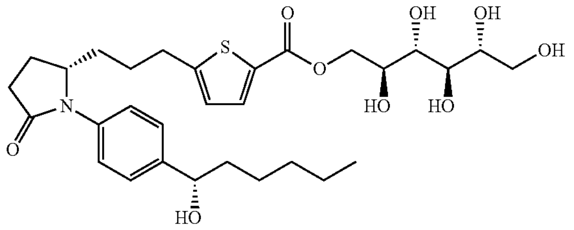

(VIl)

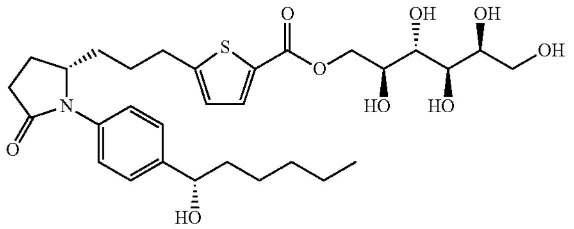

(VIm)

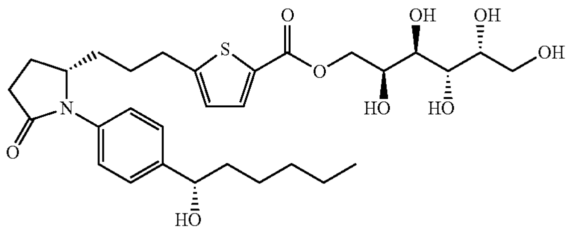

-continued (VIn)

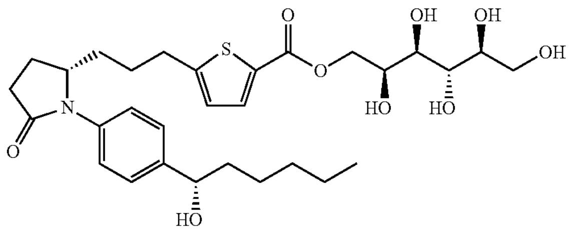

(VIo)

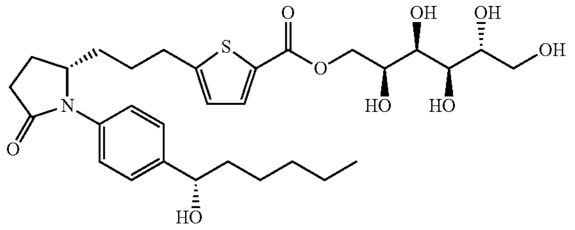

(VIp)

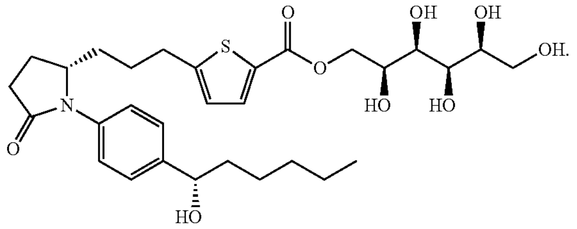

11. An ophthalmic pharmaceutical composition comprising the compound of claim 1 and an ophthalmically acceptable excipient.

12. A method of treating an ophthalmic disease in a subject, said method comprising administering a therapeutically effective amount of a compound of claim 1 to a subject in need thereof, and wherein the ophthalmic disease is selected from glaucoma and macular degeneration.

13. The method of claim 12, wherein said administering is topical ocular administering.

14. The method of claim 12, wherein said disease is glaucoma.

15. The method of claim 12, wherein said disease is macular degeneration.

16. A method of reducing corneal thickening, said method comprising administering a therapeutically effective amount of a compound of claim 1 to a subject in need thereof.

17. The method of claim 16, wherein said subject suffers from glaucoma.

18. The method of claim 16, wherein said subject suffers from ocular hypertension.

* * * * *

UNITED STATES PATENT AND TRADEMARK OFFICE

CERTIFICATE OF CORRECTION

PATENT NO. : 10,329,284 B2
APPLICATION NO. : 15/516361
DATED : June 25, 2019
INVENTOR(S) : Robert M. Burk et al.

It is certified that error appears in the above-identified patent and that said Letters Patent is hereby corrected as shown below:

In the Specification

In Column 1, Lines 53-54, delete "Optipranalol®);" and insert -- Optipranolol®); --, therefor.

In Column 1, Lines 54-55, delete "andrenergic" and insert -- adrenergic --, therefor.

In Column 1, Line 64, delete "Intraoccular" and insert -- Intraocular --, therefor.

In Column 2, Line 47, delete "hetercycloalkyl," and insert -- heterocycloalkyl, --, therefor.

In Column 4, Lines 12-13, delete "$—CH_2–CH{=}N—O\ CH_3$," and insert -- $—CH_2—CH{=}N—OCH_3$, --, therefor.

In Column 4, Lines 25-26, delete "heteroatom" and insert -- heteroatom. --, therefor.

In Column 6, Line 30, delete "$—NR—C(NR'\ R'')=NR''''$," and insert -- $—NR—C(NR'R'')=NR''''$, --, therefor.

In Column 6, Line 58, delete "$—NR''C(O)_2R', R'$," and insert -- $—NR''C(O)_2R'$, --, therefor.

In Column 9, Line 64, delete "galactunoric" and insert -- galacturonic --, therefor.

In Column 10, Line 28, delete "2d" and insert -- $2^{nd}$ --, therefor.

In Column 11, Line 65, delete "hetercycloalkyl," and insert -- heterocycloalkyl, --, therefor.

In Column 13, Line 6, delete "furnadiyl" and insert -- furandiyl --, therefor.

In Column 13, Line 17, delete "heteroalky" and insert -- heteroalkyl --, therefor.

Signed and Sealed this
Twenty-seventh Day of August, 2019

Andrei Iancu
*Director of the United States Patent and Trademark Office*

In Column 13, Line 24, delete “heteroalky” and insert -- heteroalkyl --, therefor.

In Column 16, Line 54, delete “Formulae” and insert -- Formulae: --, therefor.

In Column 18, Line 32, delete “Formulae” and insert -- Formulae: --, therefor.

In Column 25, Line 8, delete “metiparanolol,” and insert -- metipranolol, --, therefor.

In Column 25, Line 30, delete “chlolinesterase” and insert -- cholinesterase --, therefor.

In Column 25, Lines 35-36, delete “dextrophan,” and insert -- dextrorphan, --, therefor.

In Column 25, Line 36, delete “detromethorphan,” and insert -- dextromethorphan, --, therefor.

In Column 25, Lines 40-41, delete “nifedimpine,” and insert -- nifedipine, --, therefor.

In Column 25, Line 49, delete “chloprostenol,” and insert -- cloprostenol, --, therefor.

In Column 25, Lines 49-50, delete “chloprostenol,” and insert -- cloprostenol, --, therefor.

In Column 30, Line 28, delete “chromatorgraphy” and insert -- chromatography --, therefor.

In Column 32, Line 4, delete “(2S,3 S)” and insert -- (2S,3S) --, therefor.

In Column 34, Lines 28-37, delete “ 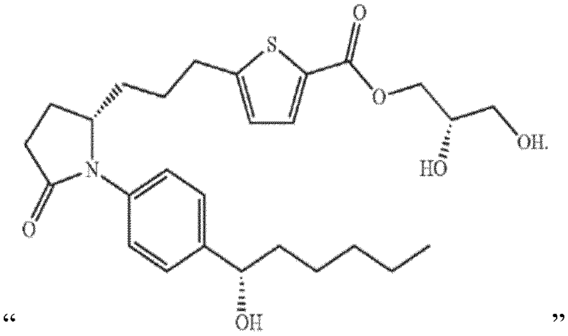 ”

and insert -- 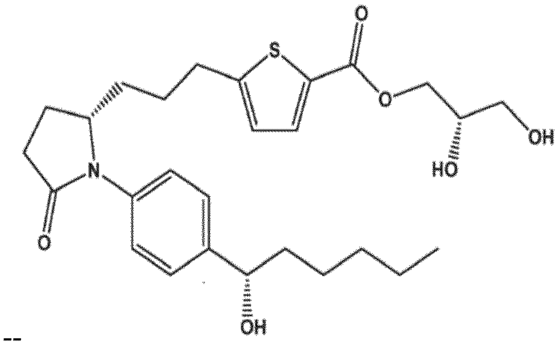 --, therefor.

In Column 36, Line 1, delete “hetercycloalkyl,” and insert -- heterocycloalkyl, --, therefor.

In Column 36, Line 9, delete "R." and insert -- $R^{1A}$. --, therefor.

In Column 38, Line 6, delete "heteroalky" and insert -- heteroalkyl --, therefor.

In Column 38, Line 13, delete "heteroalky" and insert -- heteroalkyl --, therefor.

In Column 40, Line 41, delete "(Iva)," and insert -- (IVa), --, therefor.

In the Claims

In Column 47, Lines 66-67, in Claim 2, delete "$CHOH(CH_2)_4CH_3$." and insert -- —$CHOH(CH_2)_4CH_3$. --, therefor.

In Column 49, Line 1, in Claim 6, delete "(Iva)," and insert -- (IVa), --, therefor.

In Column 51, Line 41, in Claim 10, delete "(Vii)," and insert -- (VIi), --, therefor.